US010226184B2

(12) United States Patent
Lee et al.

(10) Patent No.: US 10,226,184 B2
(45) Date of Patent: Mar. 12, 2019

(54) APPARATUS AND METHOD FOR ENHANCING ACCURACY OF A CONTACTLESS BODY TEMPERATURE MEASUREMENT

(71) Applicant: Samsung Electronics Co., Ltd., Gyeonggi-do (KR)

(72) Inventors: Min-Hyoung Lee, Gyeonggi-do (KR); Jung-Taek Oh, Seoul (KR); Jae-Geol Cho, Gyeonggi-do (KR); June-Hyeon Ahn, Gyeonggi-do (KR); Jea-Hyuck Lee, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 606 days.

(21) Appl. No.: 14/725,580

(22) Filed: May 29, 2015

(65) Prior Publication Data
US 2016/0029896 A1 Feb. 4, 2016

(30) Foreign Application Priority Data

Jul. 31, 2014 (KR) .................. 10-2014-0098488

(51) Int. Cl.
*A61B 5/01* (2006.01)
*G01J 5/08* (2006.01)
(Continued)

(52) U.S. Cl.
CPC .............. *A61B 5/01* (2013.01); *A61B 5/6898* (2013.01); *A61B 5/7203* (2013.01);
(Continued)

(58) Field of Classification Search
None
See application file for complete search history.

(56) References Cited

U.S. PATENT DOCUMENTS 8,275,413 B1\* 9/2012 Fraden .............. H04M 1/72522
455/344
2005/0117049 A1 6/2005 Suzuki
(Continued)

FOREIGN PATENT DOCUMENTS

JP 2002-027051 1/2002
JP 2010-194074 9/2010
(Continued)

OTHER PUBLICATIONS

International Search Report dated Oct. 28, 2015 issued in counterpart application No. PCT/KR2015/008009, 11 pages.
(Continued)

*Primary Examiner* — Patricia J Park
(74) *Attorney, Agent, or Firm* — The Farrell Law Firm, P.C.

(57) ABSTRACT

An electronic device for enhancing accuracy of a contactless body temperature measurement is provided. The electronic device includes a camera module for determining whether an image of an object is in focus, a temperature sensor for measuring a temperature of the object, and a processor for determining, as a temperature of the object, a temperature output from the temperature sensor corresponding to a focus matching time as a result of determining whether the image of the object is in focus.

25 Claims, 23 Drawing Sheets

(51) Int. Cl.
    *G01J 5/02*     (2006.01)
    *G01J 5/00*     (2006.01)
    *A61B 5/00*     (2006.01)
    *H04M 1/21*     (2006.01)

(52) U.S. Cl.
    CPC ............ *A61B 5/7221* (2013.01); *A61B 5/742* (2013.01); *G01J 5/0025* (2013.01); *G01J 5/025* (2013.01); *G01J 5/0265* (2013.01); *G01J 5/089* (2013.01); *G01J 5/0859* (2013.01); *G01J 2005/0077* (2013.01); *H04M 1/21* (2013.01)

(56) References Cited

U.S. PATENT DOCUMENTS

| | | | |
|---|---|---|---|
| 2009/0105605 A1* | 4/2009 | Abreu | A61B 5/0008 600/549 |
| 2011/0112791 A1 | 5/2011 | Pak et al. | |
| 2012/0150482 A1 | 6/2012 | Yildizyan et al. | |
| 2012/0218418 A1* | 8/2012 | Strandemar | G01J 5/02 348/164 |
| 2013/0204570 A1 | 8/2013 | Mendelson et al. | |
| 2013/0259087 A1 | 10/2013 | Gerlitz | |
| 2015/0156298 A1 | 6/2015 | Ikemoto et al. | |

FOREIGN PATENT DOCUMENTS

| | | |
|---|---|---|
| JP | 2011-067371 | 4/2011 |
| JP | 2011-072639 | 4/2011 |
| JP | 2011-177500 | 9/2011 |
| JP | 2011-179986 | 9/2011 |
| JP | 2012-217563 | 11/2012 |
| KR | 10-1138955 | 4/2012 |
| TW | 201410203 | 3/2014 |

OTHER PUBLICATIONS

European Search Report dated Dec. 3, 2015 issued in counterpart application No. 15178981.5-1562, 8 pages.

Taiwanese Office Action dated Dec. 3, 2018 issued in counterpart application No. 10721139670, 10 pages.

* cited by examiner

APPARATUS AND METHOD FOR ENHANCING ACCURACY OF A CONTACTLESS BODY TEMPERATURE MEASUREMENT

PRIORITY

This application claims priority under 35 U.S.C. § 119(a) to Korean Patent Application Serial No. 10-2014-0098488, which was filed in the Korean Intellectual Property Office on Jul. 31, 2014, the entire disclosure of which is incorporated herein by reference.

BACKGROUND OF THE INVENTION

1. Field of the Invention

The present invention relates generally to apparatuses and methods for measuring body temperature, and more particularly, to apparatuses and methods for enhancing accuracy of contactless body temperature measurement.

2. Description of the Related Art

Conventional thermometers come in two types: contact-type and non-contact type. Contact-type thermometers require physical contact with a target object which is to be measured. Therefore, this type of thermometer cannot give precise readings when used for, e.g., infants who seldom stay still, and if used at nighttime, this type of thermometer may disturb sleep.

In contrast, some non-contact type thermometers measure the wavelength of an infrared emission from a target object with a temperature higher than the absolute temperature to determine the temperature of the target object. This type of thermometer allows for a quick and continuous measurement, without contact, in an accurate way, even when the target is on the move, but this type of thermometer may not be as accurate, e.g., depending on measurement distances.

Commercially available digital thermometers measure temperature by receiving infrared rays from one's ear or forehead using an infrared (IR) sensor. Non-contact thermometers sometimes have a telescopic structure that keeps it at a constant distance from the region where temperature is to be measured.

Carrying a body thermometer all the time can be annoying and impractical, although it indeed comes in handy from time to time.

With increased interest in health and for more efficient health-care, technologies are being developed to provide smartphones or other portable electronic devices with diverse checkup features, e.g., for reading blood pressure, blood sugar, or body fat, and there is also an ongoing effort to provide a body thermometer in the electronic devices.

A sensor of non-contact thermometers for measuring body temperature and an object area at which a temperature is to be measured by the sensor should be spaced part from each other at a predetermined distance to give precise results of body temperature measurement.

However, the telescopic design is difficult to apply to the electronic devices due to structural limitations and variations (and resultant measurement errors) in the distance between the sensor for temperature measurement and the object area.

Although proximity sensors may be adopted for the electronic devices, the proximity sensors can only detect objects on the surface where the detection is to be carried out and the proximity sensors require additional parts, such as separate optic modules including an emitter and a receiver to implement the function.

SUMMARY OF THE INVENTION

The present invention has been made to address at least the above mentioned problems and/or disadvantages and to provide at least the advantages described below.

An aspect of the present invention provides an electronic device and method that may give correct readings for body temperature measurement in a contactless manner.

An aspect of the present invention provides an electronic device that includes camera module and method for allowing for precise body temperature measurement by keeping an object area at which a temperature is to be measured and the camera module away from each other at a constant distance so that the measurement distance remains constant.

An aspect of the present invention provides an electronic device and method that may reduce errors and deviations between measured body temperature values that may occur due to variations in the distance between a sensor of the electronic device and the object area.

In accordance with an aspect of the present invention, there is provided an electronic device for enhancing accuracy of a contactless body temperature measurement. The electronic device includes a camera module for determining whether an image of an object is in focus, a temperature sensor for measuring a temperature of the object, and a processor for determining, as a temperature of the object, a temperature output from the temperature sensor corresponding to a focus matching time as a result of determining whether the image of the object is in focus.

In accordance with an aspect of the present invention, there is provided a method for enhancing accuracy of a contactless body temperature measurement by an electronic device. The method includes determining whether an image of an object is in focus and displaying a measured temperature of the object corresponding to a focus matching time as a result of determining whether the image of the object is in focus.

BRIEF DESCRIPTION OF THE DRAWINGS

The above and other aspects, features, and advantages of certain embodiments of the present invention will be more apparent from the following detailed description taken in conjunction with the accompanying drawings, in which:

FIGS. 19A-20D are diagrams illustrating examples of body temperature measurement methods using different electronic devices, according to an embodiment of the present invention;

DETAILED DESCRIPTION OF EMBODIMENTS OF THE PRESENT INVENTION

Figure 1:
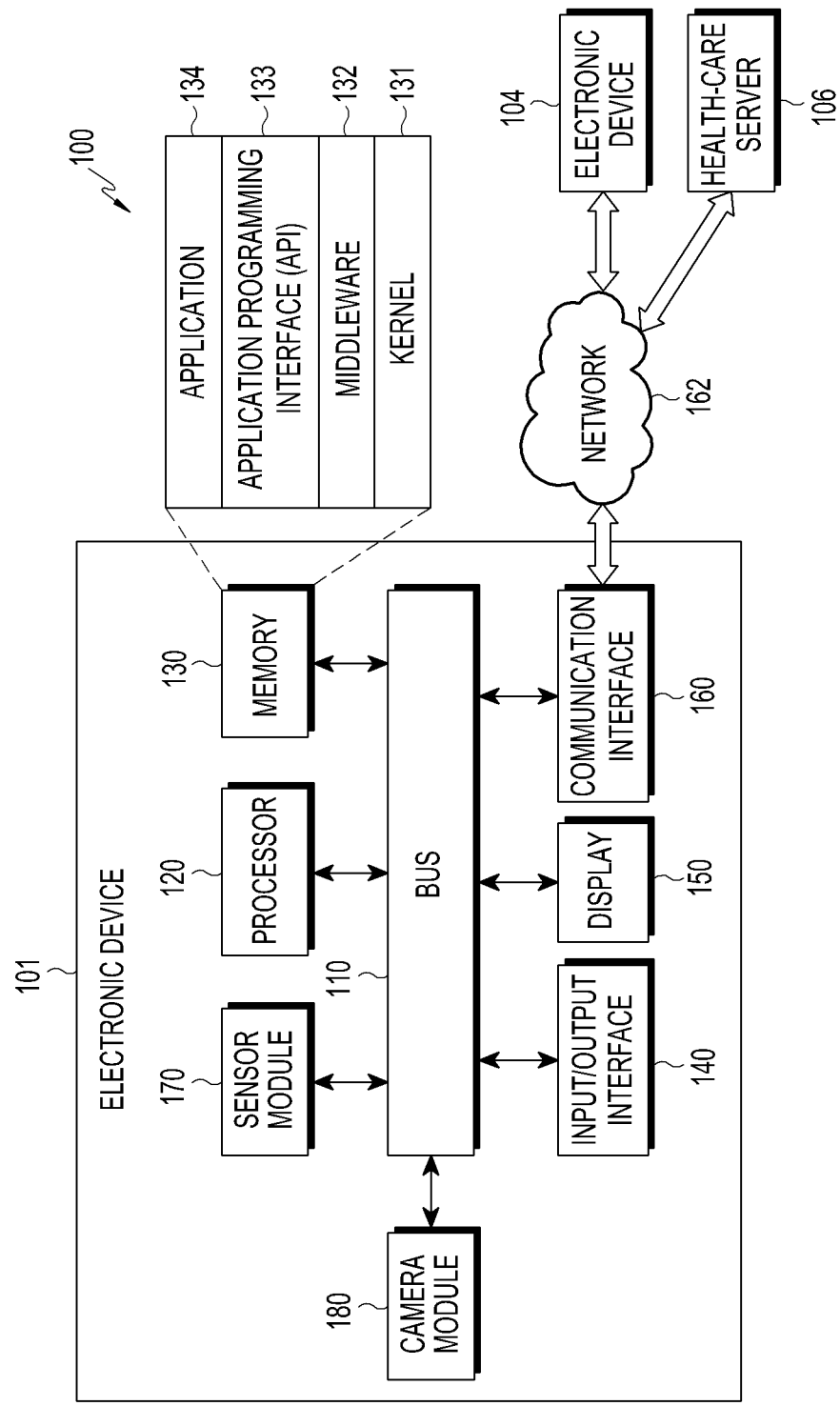
FIG. 1 is a diagram illustrating a network including an electronic device, according to an embodiment of the present invention.

Hereinafter, embodiments of the present invention are described in detail with reference to the accompanying drawings. Those of ordinary skill in the art will recognize that various changes and modifications of the embodiments described herein can be made without departing from the scope and spirit of the present invention. In addition, descriptions of well-known functions and constructions may be omitted for clarity and conciseness. The same reference symbols are used throughout the drawings to refer to the same or like parts.

It should be noted that various embodiments described below may be applied or used individually or in combination. The terms "comprise" and/or "comprising" as herein used specify the presence of disclosed functions, operations, or components, but do not preclude the presence or addition of one or more other functions, operations, or components. It will be further understood that the terms "comprise" and/or "have," when used in this specification, specify the presence of stated features, integers, steps, operations, elements, and/or components, but do not preclude the presence or addition of one or more other features, integers, steps, operations, elements, components, and/or groups thereof.

As used herein, the term "A or B" or "at least one of A and/or B" includes any and all combinations of one or more of the associated listed items. For examples, "A or B" or "at least one of A or/and B" each may include A, or include B, or include both A and B.

Ordinal numbers as herein used, such as "first", "second", etc., may modify various components of various embodiments, but do not limit those components. For example, these terms do not limit the order and/or importance of the components. These terms are only used to distinguish one component from another. For example, a first user device and a second user device are different user devices from each other. For example, a first component may be referred to as a second component, and vice versa.

When a component is "connected to" or "coupled to" another component, the component may be directly connected or coupled to the other component, or other component(s) may be provided therebetween. In contrast, when a component is "directly connected to" or "directly coupled to" another component, no other components may are provided therebetween.

The terms as used herein are provided merely to describe some embodiments of the present invention, but are not intended to limit the present invention. It is to be understood that the singular forms "a," "an," and "the" include plural references unless the context clearly dictates otherwise.

The term 'module' may refer to a unit including one of hardware, software, and firmware, or a combination thereof. The term 'module' may be interchangeably used with a unit, logic, logical block, component, or circuit. The module may be a minimum unit or part of an integrated component. The module may be a minimum unit or part of performing one or more functions. The module may be implemented mechanically or electronically. For example, according to an embodiment of the present invention, the module may include at least one of Application Specific Integrated Circuit (ASIC) chips, Field Programmable Gate Arrays (FPGAs), or Programmable Logic Arrays (PLAs) that perform some operations, which have already been known or will be developed in the future.

Unless otherwise defined, all terms including technical and scientific terms used herein have the same meaning as commonly understood by one of ordinary skill in the art to which the embodiments of the present invention belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In accordance with the present invention, an electronic device as disclosed herein may be a device with a communication function. For example, examples of the electronic device may include, but is not limited to, a smartphone, a tablet personal computer (PC), a mobile phone, a video phone, an e-hook reader, a desktop PC, a laptop computer, a netbook computer, a personal digital assistant (PDA), a portable multimedia player (PMP), an MP3 player, a mobile medical device, a camera, or a wearable device (e.g., a head-mounted device (HMD), electronic clothes, an electronic bracelet, an electronic necklace, an electronic accessory, an electronic tattoo, or a smart watch).

The electronic device may be a smart home appliance with a health-care function. For example, examples of the smart home appliance may include, but is not limited to, a television, a digital video disk (DVD) player, an audio player, a refrigerator, an air conditioner, a vacuum cleaner, an oven, a microwave oven, a washer, a dryer, an air cleaner, a set-top box, a TV box (e.g., Samsung HomeSync®, Apple TV®, Google TV®), a gaming console, an electronic dictionary, a camcorder, or an electronic picture frame The electronic device may include, but is not limited to, various medical devices (e.g., magnetic resource angiography (MRA) device, a magnetic resource imaging (MRI) device, a computed tomography (CT) device, an imaging device, or an ultrasonic device), a navigation device, a global positioning system (GPS) receiver, an event data recorder (EDR), a flight data recorder (FDR), an automotive infotainment device, an sailing electronic device (e.g., a sailing navigation device, a gyroscope, or a compass), avionics, security devices, vehicular head units, industrial or home robots, automatic teller's machines (ATMs), or point of sales (POS) devices.

The electronic device may include, but is not limited to, a piece of furniture with a health-care function, part of a building/structure, an electronic board, an electronic signature receiving device, a projector, or various measurement devices (e.g., devices for measuring water, electricity, gas, or electromagnetic waves). The electronic device may be one or a combination of the above-listed devices or appliances. The electronic device may be a flexible device. The electronic device is not limited to the above-listed devices or appliances.

As used herein, the term "user" may denote a human or another device (e.g., an artificial intelligent electronic device) using the electronic device.

FIG. 1 is a diagram illustrating a network 100 including an electronic device 101, according to an embodiment of the present invention.

Referring to FIG. 1, the electronic device 101 includes a bus 110, a processor 120, a memory 130, an input/output interface 140, a display 150, and a communication interface 160.

The bus 110 connects the other components to each other, and the bus 110 may carry communications (e.g., control messages) between the other components.

The processor 120 receives commands from other components (e.g., the memory 130, the input/output interface 140, the display 150, or the communication interface 160) through, e.g., the bus 110, interprets the received commands, and executes computation or data processing according to the interpreted commands.

The processor 120 may include the memory 130 for storing information required by the processor 120. The processor 120, as a central processing unit, controls the overall operation of the electronic device 101 and performs an operation according to a method for enhancing accuracy of contactless body temperature measurements.

The processor 120 controls a focusing operation on a portion of a body of a user (hereinafter referred to as an object), e.g., where a body temperature is to be measured, while the camera module 180 is operating in one or more modes, e.g., macro mode, and if an image of an object to be measured is focused, outputs a result of the measured body temperature. Here, a focal distance corresponds to a position that is maintained spaced apart from the portion of the object whose temperature is to be measured. If the body temperature measurement is performed at the time that a focused image is obtained, the temperature sensor and the portion of the object whose temperature is to be measured may be spaced apart from each other at a predetermined distance, thus providing a correct result of the body temperature measurement.

As an application for measuring the body temperature is executed, the camera module 180 is operated for identifying whether focus matching is achieved for an image of the object. Here, the image of the object may be an image for a portion of a forehead, where the temporal arteries are distributed, or a portion behind an ear lobe, where the temporal artery passes. The processor 120 determines, as the temperature of the object, a temperature output from the temperature sensor at the time of the focus matching, e.g., as a result of identifying whether the focus matching is achieved. The processor 120 may be configured to inform a user of the focus matching time. For example, the processor 120 may inform the user of the focus matching time through an instruction screen on the display 150 or an alert sound.

The temperature output from the temperature sensor at the focus matching time may be based on various temperature measurement modes.

For example, if the focus matching time occurs, the processor 120 measures a portion of the object whose temperature is to be measured with the temperature sensor.

Alternatively, the processor 120 consecutively measures (e.g., using the temperature sensor) the temperature of the object while the camera module 180 identifies whether the focus matching is achieved and determines, as the temperature of the object, the temperature measured corresponding to the focus matching time from, among temperatures that were consecutively measured.

For example, the processor 120 consecutively measures the temperature of the portion of the object whose temperature is to be measure through the temperature sensor, with a preview used to show the image of the portion of the object whose temperature to be measured through the camera module 180, while the user brings the electronic device 101 closer or away from the portion of the object whose temperature is to be measured, in a direction perpendicular to the portion of the object whose temperature is to be measured.

The processor 120 determines, as the temperature of the portion of the object whose temperature is to be measured, a measured value corresponding to the time that the image is in focus from among values consecutively measured, and the processor 120 displays the result of the body temperature measurement. Identifying whether the image is in focus or not may be performed by the processor 120 or an image signal processor, which is described greater detail below.

The memory 130 stores a command or data received from the other components (e.g., the input/output interface 140, the display 150, or the communication interface 160) or a command or data generated by the processor 120 or other components. The memory 130 retains programming modules including, e.g., a kernel 131, middleware 132, an application programming interface (API) 133, or an application 134. The programming modules may be configured in software, firmware, hardware or a combination of two or more thereof.

The kernel 131 controls or manages system resources (e.g., the bus 110, the processor 120, or the memory 130) used to execute the operation or function implemented in the other programming modules, e.g., the middleware 132, the API 133 or the application 134. The kernel 131 provides an interface that allows the middleware 132, the API 133, or the application 134 to access the individual components of the electronic device 101 to control or manage the electronic device 101.

The middleware 132 may function as a relay to allow the API 133 or the application 134 to communicate data with the kernel 131. A plurality of applications 134 may be provided. The middleware 132, in response to work requests received from the applications 134, allocates a priority of using the system resources of the electronic device 101 (e.g., the bus 110, the processor 120, or the memory 130) to at least one of the plurality of applications 134 in relation to the work requests.

The API 133 is an interface that allows the application 134 to control functions provided from the kernel 131 or the middleware 132. For example, the API 133 may include at least one interface or function (e.g., a command) for filing control, window control, image processing or text control.

There may be provided a plurality of applications 134 including, but not limited to, a short message service/multimedia message service (SMS/MMS) application, an email application, a calendar application, an alarm application, a health-care application (e.g., as application for monitoring a body temperature measurement state, measuring quantity of motion or blood sugar), or an environmental information application (e.g., an application providing atmospheric pressure, moisture, or temperature information). Further, the application 134 may be an application related to information exchange between the electronic device 101 and an external electronic device (e.g., electronic device 104). Examples of the information exchange-related application may include, but is not limited to, a notification relay application for transferring specific information to the external electronic device, or a device management application for managing the external electronic device.

For example, in the case of the health-care application, the user may execute the health-care application to access a health-care server 106 or the electronic device 104.

The user may measure bio information using a bio sensor included in the sensor module 170.

The electronic device 101 transmits a measurement value of the bio information to the electronic device 104 or the health-care server 106 through the communication interface 160. In the instance where the electronic device 101 transmits the measurement value to the health-care server 106, the electronic device 101 obtains a diagnosis result for the measurement value from the health-care server 106 and displays the diagnosis result on the display 150 or provides the same to the user through, e.g., an alert sound or voice message. The measured body temperature value may be transmitted to the health-care server 106 or the electronic device 104 using a temperature sensor, and information corresponding to the measured body temperature value may be output to a user, another module of the electronic device 101, the electronic device 104, or another electronic device.

The electronic device 104 receives the measured body temperature value or a captured image from the electronic device 101, collects, generates, manages, provides, or processes the information corresponding to the measured body temperature value, and sends the result back to the electronic device 101. The electronic device 104 may be configured to be similar to the electronic device 101. For example, the electronic device 104 may include at least one of a communication interface 160 for communicating with the electronic device 101, the sensor module 170 for measuring a body temperature, and the camera module 180 for taking a picture of a body portion where a body temperature is to be measured, as well as the processor 120 to perform a contactless body temperature measuring function in the electronic device 101.

The applications 134 may include an application designated according to an attribute (e.g., type of the electronic device) of the external electronic device 104. Further, the applications 134 may include at least one of an application designated to the electronic device 101 or an application received from an external electronic device (e.g., the health-care server 106 or the electronic device 104).

The input/output interface 140 transfers commands or data input by the user through an input/output device (e.g., a keyboard or touchscreen) to the processor 120, the memory 130, or the communication interface 160 through, e.g., the bus 110. For example, the input/output interface 140 provides data for an input, such as the user's finger or an electronic pen, input through the touchscreen, to the processor 120.

An input unit of the input/output interface 140 may include a touch panel, a digital pen sensor, a key, or an ultrasonic input device. The touch panel may recognize touch inputs in at least one of capacitive, resistive, infrared, or ultrasonic methods. The touch panel may be implemented using at least one or more panels that may sense various inputs, such as a user's single or multi-touch input, a drag input, a handwriting input, or a drawing input, using various objects, such as a finger or pen.

For example, the touch panel may be implemented using a single panel that may sense both a finger input and a pen input or using two panels including a touch recognition module that may sense a finger input and a pen recognition module that may sense a pen input. Further, the touch panel may further include a control circuit. With the capacitive method, physical contact or proximity detection may be possible. The touch panel may further include a tactile layer. In this regard, the touch panel may provide the user with a tactile response. The input/output interface 140 may output, through the input/output device (e.g., a speaker or display), commands or data received from the processor 120, the memory 130, or the communication interface 160 through, e.g., the bus 110.

The display 150 displays various types of information (e.g., multimedia data or text data) to the user. Further, the display 150 displays a preview image that allows the user to identify the position of an object whose temperature is to be measured or whether focus matching is achieved in order to measure the temperature of the object, and a target for body temperature measurement, under the control of the processor 120. Further, the display 150 displays an instruction screen that allows the user to adjust the distance between the object whose temperature is to be measured and the electronic device 101 and the measured position. Further, the display 150, when in focus, displays a measured body temperature result screen including the measured temperature. The display 150 may be implemented as a touchscreen.

The measured body temperature result may be displayed on the screen through various indicators. For example, the indicators may be represented in various forms, such as a character indicating normal or an indicator indicating a warning. Further, upon measuring the body temperature, an indicator may be displayed on the screen to indicate if the prerequisites for taking a temperature measurement are met.

For example, if the user tries to measure the body temperature, with the electronic device 101 placed at a wrong position, the processor 120 may provide the user with instruction information for the user to relocate the electronic device 101 to a correct position for the temperature measurement, e.g., a position where an artery passes between the user's eyebrows. Such instruction information may be displayed as an image on the display 150 or may be provided to the user through a vibration or audio.

Further, the display 150 displays the state of executing the body temperature measurement in body temperature measurement mode according to the execution of body temperature measurement. For example, when the body temperature measurement mode operable, the body temperature measurement execution state may be displayed on the display 150.

The touchscreen may be provided with a display panel for displaying information output from the electronic device 101 and an input panel for receiving various inputs by the user. The display panel may be a panel, such as, e.g., an LCD or AMOLED.

The display panel may display various screens according to various states of the electronic device 101, applications being executed by the electronic device 101, and services provided the electronic device 101.

The input panel may be implemented using one or more panels that may sense various inputs, such as a user's single or multi-touch input, a drag input, a handwriting input, or a drawing input, using various objects, such as a finger or pen. For example, the input panel may be implemented using a single panel that may sense both a finger input and a pen input or using two panels including a touch recognition module that may sense a finger input and a pen recognition module that may sense a pen input.

The touchscreen may output, to a touchscreen controller, a signal corresponding to at least one user input to a user graphic interface. The touchscreen may receive at least one user input through the user's body (e.g., an index finger or other finger). The touchscreen may receive a continuous motion of a touch. The touchscreen may output an analog signal corresponding to the continuous motion of the input touch to the touchscreen controller.

The touch is not limited to contact between the touchscreen and a user input means, such as a finger, and rather may include non-contact (for example, in the instance where the user input device is positioned within a recognizable distance (e.g., 1 cm) where the user input means may be detected without direct contact with the touchscreen). The distance or interval within which the user input device may be recognized on the touchscreen may be varied depending on the performance or structure of the electronic device 101. In particular, the touchscreen may be configured to output a value detected by a direct touch event (e.g., by contact of the user input device to the touchscreen) and a value (including, e.g., a voltage value or current value as an analog value) detected by an indirect touch event (i.e., a hovering event), which are different from each other, so that the direct touch event and the hovering event may be detected distinct from each other.

The touchscreen may be implemented in a capacitive, infrared, or acoustic wave manner, or in a combination thereof.

A touchscreen controller converts a signal input from the touchscreen into a digital signal and transmits the digital signal to the processor 120. The processor 120 controls a user interface displayed on the touchscreen using the digital signal received from the touchscreen controller. For example, the processor 120 may allow a shortcut icon displayed on the touchscreen or object to be selected or executed in response to the direct touch event or hovering event. Further, the touchscreen controller may be integrated with the processor 120.

The touchscreen controller may identify a hovering interval or distance as well as a position of the user's input by detecting a value (e.g., a current value) output through the touchscreen and may convert the identified distance value into a digital signal (e.g., an identified distance value along the Z axis) and provide the digital signal to the processor 120.

The communication interface 160 provides an interface for communication between the electronic device 101 and an external electronic device (e.g., the electronic device 104 or the health-care server 106). For example, the communication interface 160 may be wiredly or wirelessly connected with the network 162 to communicate with the electronic device 104. The wireless connection may be made by various radio communication protocols, including, but not limited to, wireless fidelity (WiFi), Bluetooth (BT), near field communication (NFC), GPS, or cellular communication protocols (e.g., long term evolution (LTE), LTE advanced (LTE-A), code division multiple access (CDMA), wideband CDMA (WCDMA), universal mobile telecommunication system (UMTS), wireless broadband (WiBro) or global system for mobile communication (GSM)). The wired connection may be made by various wired communication protocols, including, but not limited to, universal serial bus (USB), high definition multimedia interface (HDMI), recommended standard 232 (RS-232), or plain old telephone service (POTS).

The electronic device 101 may be connected with the health-care server 106 through the network 162. The electronic device 101 transmits a result of a body temperature measurement to the health-care server 106 and obtains information created based on the result of the body temperature measurement from the health-care server 106.

Further, the electronic device 101 analyzes, works or processes bio information of the measured target, e.g., a result of monitoring the body temperature in real-time, and outputs the result while simultaneously transmitting the result to the health-care server 106, allowing a result of diagnosis or prescription according to the result to be output.

Further, the electronic device 101 accumulates results of body temperature measurements for a predetermined period necessary for health diagnosis and stores the accumulated body temperature data in the memory 130. The accumulated body temperature data may be transmitted to the health-care server 106. The health-care server 106 may provide support for health related information, diagnosis results, searching for various medical information, promotion of a customers' health, self-diagnosis, medical service appointments, comparing and evaluating various products, and information on clinics, based on the received body temperature data.

In the instance where the diagnosis result shows an emergency, the health-care server 106 or the electronic device 101 informs the user of the emergency so that the user may take emergency measures. As such, the health-care server 106 collects, generates, stores, provides, or processes information on the body temperature measurement and sends the result back to the user through the electronic device 101.

The network 162 may be a telecommunication network. The telecommunication network may include a computer network, the Internet, an Internet of Things (IoT) network, or a telephone network. Protocols for communication between the electronic device 101 and the external electronic device (examples of such protocols include, but not limited to, transport layer protocol, data link layer protocol, or physical layer protocol) may be supported by the application 134, the API 133, the middleware 132, the kernel 131, or the communication interface 160.

The sensor module 170 includes at least one sensor for detecting the state of the electronic device 101. For example, the sensor module 170 includes at least one sensor, such as a proximity sensor for detecting when a portion of the body approaches the electronic device 101, an illumination sensor for detecting an amount of light around the electronic device 101, a motion sensor for detecting a motion of the electronic device 101 (e.g., rotation, acceleration or vibration of the electronic device 101), a gyroscope for detecting a rotational movement of the electronic device 101, an acceleration meter for detecting an accelerated movement of the electronic device 101, a geo-magnetic sensor for detecting a point of a compass of the electronic device 101 using the geo-magnetic field, a gravity sensor for detecting a direction of the gravity, or an altimeter for detecting an altitude by measuring the atmosphere pressure.

Further, the sensor module 170 may include a bio sensor. The bio sensor is a sensor for measuring bio information. The bio sensor may include at least one temperature sensor for measuring the temperature of a portion of an object within a predetermined distance. For the user to measure their own temperature, the temperature sensor may be disposed on the front surface of the electronic device 101 so that the user may measure the temperature of a portion of the body of the user for measurement while simultaneously identifying the portion for measurement by viewing the screen displayed on the display 150. In the instance where the user wants to measure a temperature of another person (e.g., with the electronic device 101 in his hand), such as an infant, the temperature sensor may be disposed on the rear surface of the electronic device 101 so that the user may measure the temperature of a portion of a body at which a temperature is to be measured while simultaneously identifying that portion for measurement by viewing the screen displayed on the display 150. A plurality of temperature sensors may be provided and disposed at positions adjacent to the front camera and rear camera. As such, the temperature sensor may be disposed at a position adjacent to the camera module 180, but the position where the temperature sensor is disposed is not limited thereto.

The temperature sensor may convert wavelength information, obtained by measuring an infrared wavelength emitted from the object whose temperature was measured with a temperature greater than or equal to an absolute temperature, into a temperature and may output the converted temperature. The temperature sensor may be an infrared sensor that measures temperature by radiating an infrared beam to a portion of the object whose temperature is to be measured at a predetermined distance spaced apart from the object. The predetermined distance may be a focal distance between the camera module 180 and a portion of the object whose temperature is to be measured. Such a temperature sensor may also output an average of the temperature values obtained through wavelengths measured by repetitively radiating infrared beams to the portion of the object whose temperature is to be measured. For example, the average of the temperature values may be an average of temperature values measured within one second.

An example of a portion of the object whose temperature is to be measured may be the surface of the forehead, where the temporal arteries are distributed. The temperature sensor may measure body temperature from the amount of infrared light generated passing through the temporal arteries distributed in the forehead, which reflect the body temperature. Another example of a portion of the object whose temperature is to be measured may be a portion behind an ear lobe where the temporal artery passes. As such, the temperature sensor may calculate the body temperature by measuring the temperature of the portion where the temporal arteries are distributed.

The camera module 180 includes a first camera and a second camera for capturing a still image or video under the control of the processor 120. Further, the camera module 180 includes at least one of a telescopic body part for performing zoom-in or zoom-out for taking a picture of the object whose temperature is to be measured, a motor part for controlling the movement of the telescopic body part, and a flash, which can be used as an auxiliary light source necessary for taking a picture of the object whose temperature is to be measured. The first camera, may be disposed on the front surface of the electronic device 101, and the second camera may be disposed on the rear surface of the electronic device 101.

The first and second cameras each include a lens system and an image sensor. The first and second cameras each converts a light signal input through the lens system into an electric image signal (e.g., a digital image) and outputs the converted signal to the processor 120, and the user identifies the video or still image received through the first and second cameras or take a picture or video using the first and second cameras.

The camera module 180 is configured to adjust the distance between the lens module and an imaging device disposed behind the lens module in order to provide a macro function upon obtaining a preview image of the portion of the object whose temperature is to be measured. Upon obtaining the preview image of the portion of the whose temperature is to be measured, the lens module moves forward, away from the imaging device, allowing for the portion of the object whose temperature is to be measured is displayed to be positioned within the minimum distance of the lens module.

The camera module 180 outputs a preview image for the portion of the body at which a temperature is to be measured when outputting an image for identifying the portion of the body at which a temperature is to be measured. In other words, the preview image for identifying whether focus matching is achieved is output rather than image capturing being performed to record or store an actual image of the object whose temperature is to be measured in the memory 130. As such if the temperature sensor and/or camera module 180 is operated, the sensing data output from the temperature sensor and the preview image from the camera module 180 may be temporarily stored in the memory 130 before it is determined whether focusing is achieved.

Each of the aforementioned components of the electronic device 101 may include one or more parts, and the name of each part may vary depending on the type of the electronic device 101. The electronic device 101 may include at least one of the aforementioned components, omit some of them, or include other additional component(s). Some of the components may be combined into an entity, but the entity may perform the same functions as the components. According to an embodiment of the present invention, at least a part of the electronic device 101 (e.g., modules or their functions) or method of use of the electronic device 101 (e.g., operations) may be implemented as instructions stored in a computer-readable storage medium e.g., the memory 130. The instructions, when executed by one or more processors (e.g., the processor 120), may cause the one or more processors to carry out a corresponding function.

The computer-readable storage medium may include a hardware device that is configured to store and perform program instructions (e.g., programming module), such as magnetic media such as hard discs, floppy discs, and magnetic tapes, optical media such as compact disc ROMs (CD-ROMs) and digital versatile discs (DVDs), magneto-optical media such as floptical disks, ROMs, RAMs, Flash Memories, and/or the like. Examples of the program instructions may include not only machine language codes but also high-level language codes which are executable by various computing means using an interpreter. The aforementioned hardware devices may be configured to operate as one or more software modules to carry out embodiments of the present invention, and vice versa.

Figure 2:
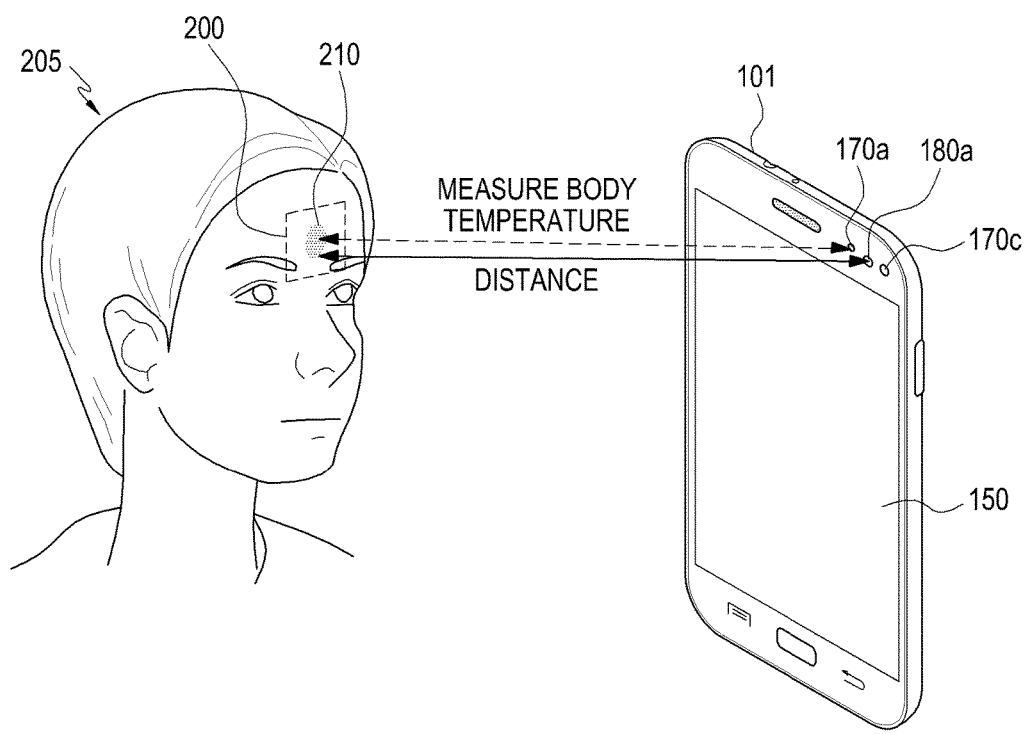
FIG. 2 is a diagram illustrating an example of a contactless body temperature measurement method using a front surface of an electronic device, according to an embodiment of the present invention.

FIG. 2 is a diagram illustrating an example of a contactless body temperature measurement method using a front surface of the electronic device 101, according to an embodiment of the present invention, Referring to FIG. 2, a first camera 180*a*, a temperature sensor 170*a*, and an illumination sensor 170*c* are disposed at an upper side on a front surface of the electronic device 101. The temperature sensor 170*a* radiates an infrared beam to a portion of an object of the body 205, e.g., a central forehead 210 between the eyebrows of a user, and the first camera 180*a* outputs an image for a forehead portion 200 of the object of the body 205.

With the first camera 180*a* and the temperature sensor 170*a* disposed on the front surface of the electronic device 101, as shown in FIG. 2 the user is able to easily measure their own body temperature. The user may identify a result of the temperature measurement of the portion of the body while simultaneously identifying that the portion of the body on the screen of the display 150. Since the user can view the screen of the display 150 while measuring his body temperature, the user may identify whether there are foreign substances, such as hairs or sweat, on his forehead, thus preventing a measurement error that may occur due to the foreign substances.

The electronic device 101 identifies whether the electronic device 101 is spaced apart from the portion of the body at which a temperature is to be measured at a predetermined distance using a macro function of the first camera 180*a*, thereby outputting a macro image. That is, the electronic device 101 outputs a focused macro image by adjusting the focal distance of the lens of the first camera 180*a*. At this time, the macro image displayed on the screen of the display 150 may be a preview image showing a preview for the portion of the object whose temperature is to be measured, but not an actual photographed image.

The predetermined distance is the focal distance between the first camera 180*a* and a portion of the object in a macro mode of the first camera 180*a*. Further, the focal distance is equal to a minimum distance from the lens to the portion of the object whose temperature is to be measured. Although the focal distance in macro mode may range from about 8 cm to about 10 cm, the focal distance may vary depending on the types of lens.

Focusing the forehead portion 200 of the portion of object, at a predetermined distance d (which is measured in cms) as shown in FIG. 2, for each measurement reduces errors or deviations between measured values. Accordingly, the measurement accuracy may be enhanced. Further, the electronic device 101 does not need a separate sensor for distance measurement to keep the electronic device 101 spaced apart from the object of the body, thereby allowing a user to measure their body temperature at the convenience of the user. Further, providing the electronic device 101 with the camera module 180 and the display 150 for contactless temperature measuring may save a user the cost of having to purchase a separate contactless temperature measuring device.

A contrast-based focusing scheme using a contrast ratio of a preview image of the portion of the object whose temperature is to be measured may be used as a focusing method. Specifically, upon executing the body temperature measurement function, the electronic device 101 may activate the first camera 180*a* and set it to macro mode, e.g., moving the lens in the first camera 180*a* to a position closest to the object whose temperature is to be measured in an optic axis direction, in order to comply with the macro focal distance.

The user may adjust the distance between the electronic device 101 and their forehead portion 200 by bringing the electronic device 101 closer to or farther away from the forehead portion 200 while the electronic device 101 is set to the macro mode. At this time, the electronic device 101 continues to detect whether focusing is achieved using the contrast of the image of the object whose temperature is to be measured. In the instance where the distance from the forehead to the electronic device 101 corresponds to the macro focal distance, the contrast of the image of the object may be maximized and may be detected as being in-focus. If the image is detected as being in-focus, the distance between the electronic device 101 and the forehead portion 200 is determined to correspond to the macro focal distance, and the temperature measured at the time of the determination is determined as the temperature of the object whose temperature is to be measured. Upon the image being in-focus, an alert may be output to inform the user that the distance is proper for measuring body temperature. The alert may be in the form of a visual alert, an auditory alert, and a tactile alert provided through a display on the display 150, a sound through a speaker of the electronic device 101, or a vibration through a vibration motor of the electronic device 101, respectively.

Figure 3:
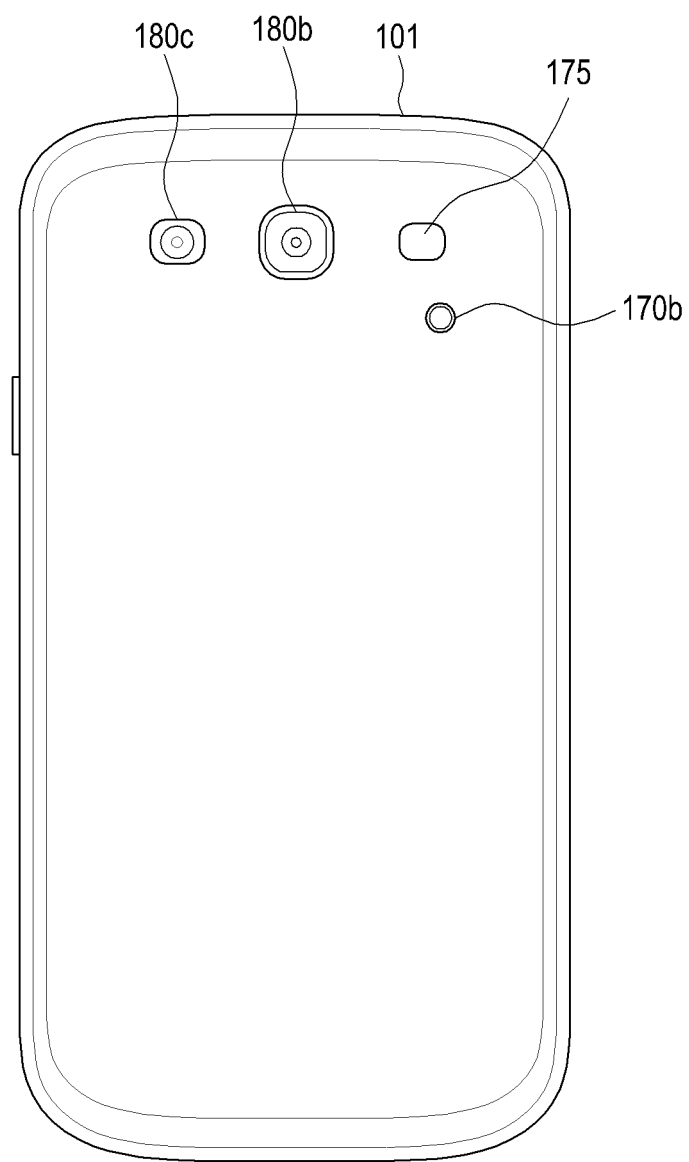
FIG. 3 is a rear end view illustrating an electronic device, according to an embodiment of the present invention.

FIG. 3 is a rear end view illustrating the electronic device 101, according to an embodiment of the present invention.

Referring to FIG. 3, a second camera 180*b*, a flash 180*c*, a speaker 175, and a temperature sensor 170*b* are disposed on the rear surface of the electronic device 101. Disposing the second camera 180*b* and the temperature sensor 170*b* on the rear surface of the electronic device 101, as shown in FIG. 3, may facilitate a user when the user has difficulty measuring his body temperature on his own.

For example, in the instance where an infant's temperature needs to be taken, the user can simultaneously identify a portion of the body at which a temperature is to be measured while viewing the screen on the display 150, with the electronic device 101 in the users' hand.

Although the temperature sensors 170*a*, 170*b* are shown disposed adjacent to the first camera. 180*a* and/or second camera 180*b* of the electronic device 101, the position of where the temperature sensors 170*a*, 170*b* are disposed on the electronic device 101 is not limited thereto. Since a position of where the first and second cameras 180*a*, 180*b* are located on the electronic device 101 may vary depending on the type of the electronic device, the temperature sensors 170*a*, 170*b* may be disposed at different positions corresponding to the positions of the first and second cameras 180*a*, 180*b*. In any event, the temperature sensors 170*a*, 170*b* and the first and second cameras 180*a*, 180*b* are disposed at positions where temperature measurement is possible while previewing the object whose temperature is to be measured.

Figure 4:
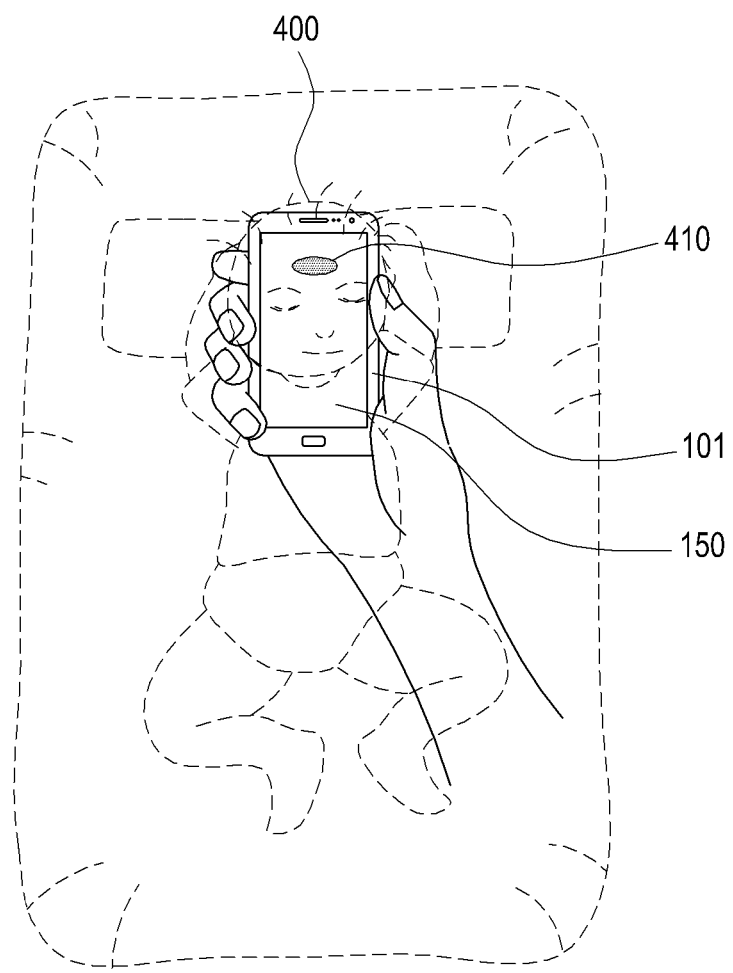
FIG. 4 is a diagram illustrating an example of a contactless body temperature measurement method using a rear surface of an electronic device, according to an embodiment of the present invention.

FIG. 4 is a diagram illustrating an example of a contactless body temperature measurement method using a rear surface of the electronic device 101, according to an embodiment of the present invention.

A user can measure a body temperature of a sleeping infant 400 as shown in FIG. 4. More particularly, a facial image of the infant 400 may be displayed on the display 150 as the user brings the electronic device 101 close to a forehead of the infant 400. In such case, the user may measure the body temperature of the infant while identifying whether the central forehead comes within a predetermined position 410 displayed on the display 150. The user can view the facial image of the infant 400 displayed on the display 150, thereby facilitating a user in taking a temperature of the infant, or a mobility impaired patient.

In an instance where a portion for measurement of the infant 400 is out of focus, a blurred image is displayed on the display 150, and in an instance where a portion for measurement is in focus, a focused image is displayed on the display 150. Accordingly, the user may identify how close or far they should bring the electronic device 101 to from the forehead of the infant 400, thereby facilitating a distance adjustment needed for taking a body temperature measurement, thereby allowing for precise body temperature measurement at a predetermined distance away from the infant.

Figure 5:
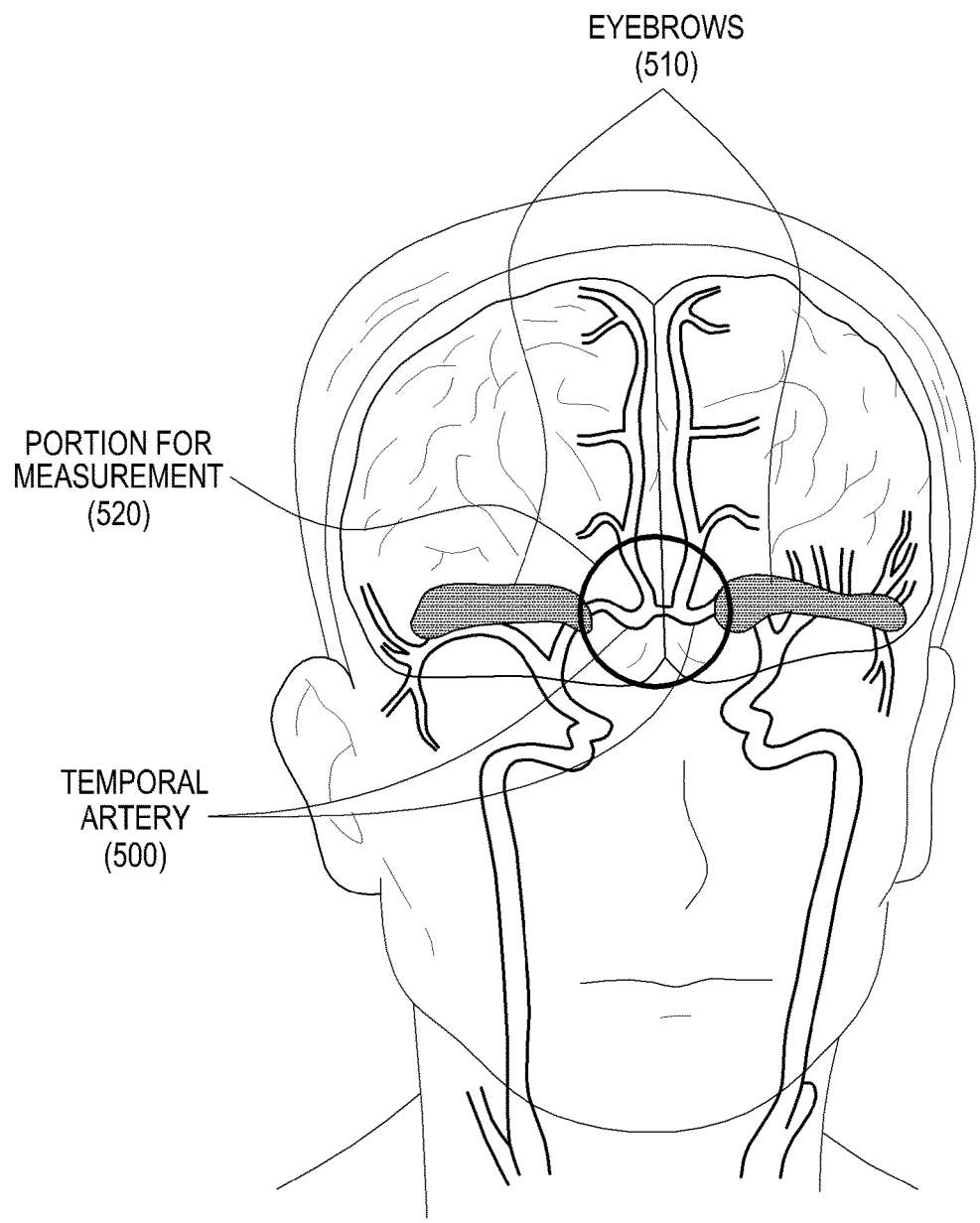
FIGS. 5 and 6 are diagrams illustrating portions of a body which may be measured using the electronic device, according to embodiments of the present invention.
Figure 6:
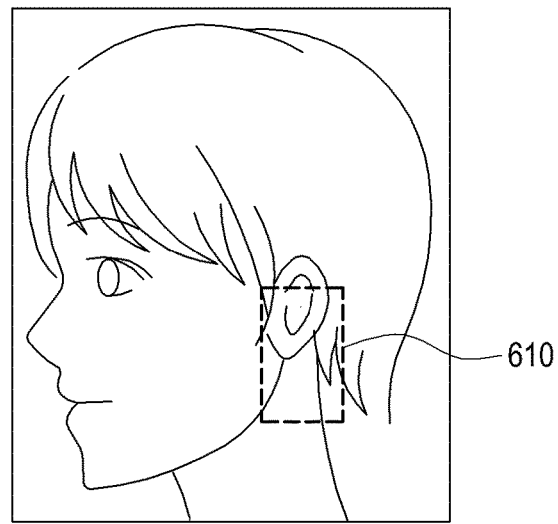

FIGS. 5 and 6 are diagrams illustrating portions of a body which may be measured using the electronic device 101, according to embodiments of the present invention.

First, referring to FIG. 5, a temporal artery 500 is an artery closest to the skin of the human body. The temporal artery 500 extends inside of the head near the temples, widely distributed under the forehead. When one has a fever, one can place their hand on the forehead to measure their body temperature, e.g., from the temporal artery 500, through which blood best reflecting body temperature passes.

When the blood flow reflecting body temperature passes through the temporal artery 500, infrared light emissions are generated, and body temperature is measured based on the amount of the infrared emissions. A contactless temperature sensor, e.g., the temperature sensor 170a, 170b, of the electronic device 101, measures the temperature of a portion of the forehead located between the eyebrows 510.

Further, the contactless temperature sensor can be configured to measure a body temperature when the contactless temperature sensor is spaced apart from behind an ear lobe, as shown in FIG. 6. In this instance, a user can take a person's temperature using the electronic device 101 from behind a person's ear lobe, where the temporal artery 500 extends. Thus, a portion 610 located behind a person's ear lobe may also serve as a point on a person's body for measuring a person's temperature.

When measuring a body temperature of another person, e.g., an infant or patient, the electronic device 101 can display an image of a portion of the object whose temperature is to be measured on the screen of the display 150. The image of the object may be, for example, at least part of an ear shape. Accordingly, the electronic device 101 may analyze the image displayed on the screen as a preview image, which may be temporally stored in the memory 130 of the electronic device 101 to determine whether at least part of the ear shape is included in the preview image.

If an input image corresponding to an area from behind the ear is input through the camera module 180, the electronic device 101 may adjust a measured position from behind the ear by referencing the preview image of the ear shape stored in the memory 130 and making a comparison with the input image. The user may identify a portion for measurement from behind the ear while viewing the image displayed on the display 150. The user may identify a result of the temperature measurement on the portion from behind the ea by using the temperature sensor 170b disposed on the rear surface of the electronic device 101, while simultaneously identifying the portion for measurement.

Figures 7A, 7B:
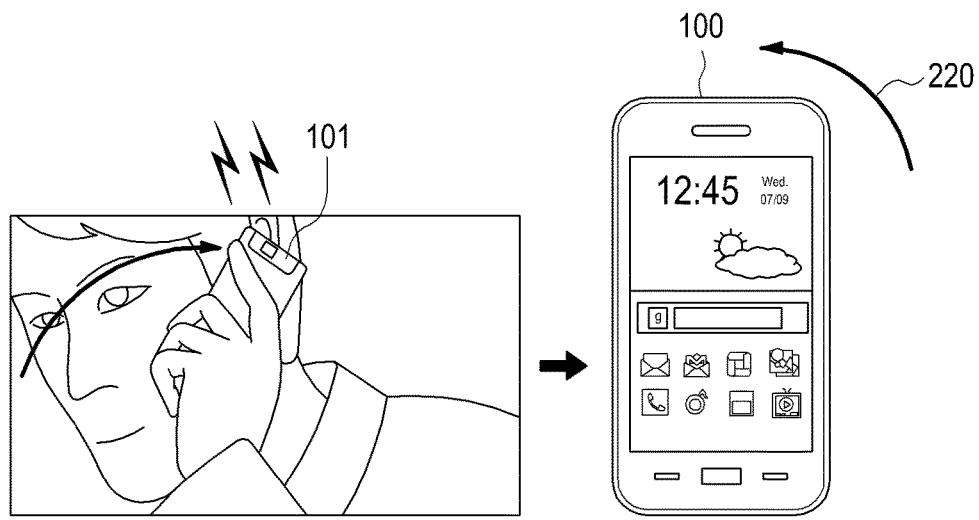
FIGS. 7A and 7B are diagrams illustrating an example of a contactless body temperature measurement method on an ear, according to an embodiment of the present invention.

FIGS. 7A and 7B are diagrams illustrating an example of a contactless body temperature measurement method on an ear, according to an embodiment of the present invention.

FIG. 7A illustrates an example in which the user brings the electronic device 101 adjacent to their ear, with the electronic device 101 in their hand, in order to measure their own body temperature. At this time, upon input of a body temperature measurement request the electronic device 101, in macro mode, performs the operation of continuously receiving macro images, even though no preview image for the ear is displayed on the display 150, and identifying whether there is an in-focus image from among the images received.

However, in the instance where the user brings the electronic device 101 close to his ear as shown in FIG. 7A, the user may have difficulty identifying the image (indicated by arrow 220 in FIG. 7B) for the their ear and the distance from the ear through the display 150. In such case, the user may be instructed as to whether the body temperature measurement is complete, through an alert sound, an instruction voice, or a haptic effect. To this end, the electronic device 101 may further include a haptic module.

The haptic module generates various tactile effects that may be felt by the user. A representative example of the haptic effects generated by the haptic module is a vibration. The strength and pattern of the vibration generated by the haptic module may be controlled. For example, different vibrations may be output, synthesized together or sequentially. The haptic module may be implemented to allow the user to feel the tactile effects through muscular senses, e.g., his finger or arm, when the electronic device 101 is positioned at a predetermined distance (i.e., the focal distance) away from the ear, with the electronic device 101 in the user's hand. Whether the minimum distance from the portion for measurement behind the ear meets the focal distance may be reported to the user by varying the strength and pattern of vibrations generated by the haptic module.

As described above, the camera module 180 generates a preview image previewing an image of the portion of the object whose temperature is to be measured and determines whether the preview image in focus using the image of the object whose temperature is to be measured. The operation of the camera module 180 is described in detail with reference to FIG. 8.

Figure 8:
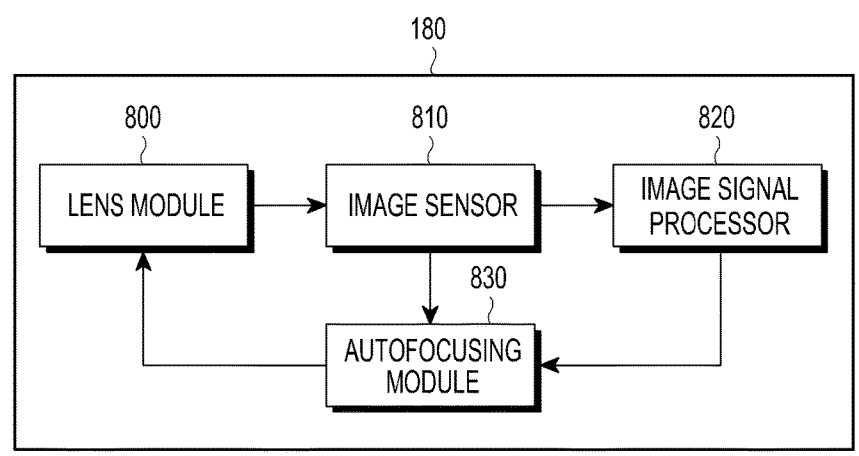
FIG. 8 is a block diagram illustrating components of a camera module, according to an embodiment of the present invention.

FIG. 8 is a block diagram illustrating components of the camera module 180, according to an embodiment of the present invention.

Referring to FIG. 8, the camera module 180 includes a lens module 800, an image sensor 810, an image signal processor 820, and an autofocusing module 830. FIG. 8 illustrates only components related to embodiments of the present invention, and other components, e.g., an image pre-processing unit, than the above-listed components in FIG. 8 may also be included. Further, although FIG. 8 illustrates an example in which the image signal processor 820 is included in the camera module 180, the image signal processor 820 may be included in the processor 120.

According to an embodiment of the present invention, a body temperature measurement should be performed within a predetermined distance in order to measure a portion of the object whose temperature measurement is to be measured in a contactless manner.

The user may request to initiate a body temperature measurement operation by executing an application for body temperature measurement in the electronic device 101. While the application is being executed, the camera module 180 may be operated in the macro mode.

The lens module 800 may be embedded and disposed on a front side of the camera module 180. The lens module 800 may have a focus lens. The focus lens performs a function of focusing the object whose a temperature is to be measured. The focus lens may be set for its current position while autofocusing mode is in execution. At this time, the focus lens is repositioned in macro mode. Here, the interval between the center of the focus lens of the lens module 800 and the image sensor 810, where an image is formed, may be said to be the focal distance.

The camera module 180 may be executed in response to the body temperature measurement request. The autofocusing module 830 of the camera module 180 may switch to macro mode by adjusting the focal distance of the lens module 800 to the minimum distance under the control of the image signal processor 820. Or, the autofocusing module 830 may be controlled by the processor 120. In macro mode, the autofocusing module 830 may calculate the focal position based on an image signal output through the image sensor 810 and may control the lens module 800 based on the result of the calculation. Accordingly, the position of the lens module 800 is monitored by the autofocusing module 830, thereby allowing for a feedback control.

The camera module 180 includes the image sensor 810. The image sensor 810 is an electronic sensor that may sense light reflected, by the object whose temperature is to he measured, through the lens module 800 and outputs an electric image signal corresponding to the sensed light. The image sensor 810 outputs image signals for the object whose temperature is to be measured on a per-frame basis. The image sensor 810 may be in the form of a complementary metal oxide semiconductor (CMOS) sensor, a charge coupled device (CCD) sensor, a foveon sensor, and complementary image sensor.

Further, the camera module 180 may further include an image buffer module for storing images formed based on the image data from the image sensor 810 on a per-frame basis.

The image signal processor 820 receives image data in real-time received by the image sensor 810 and processes the image data to comply with the screen characteristics (e.g., size, image quality, or resolution) of the display 150 or screen characteristics of other display units. A preview image image-processed may displayed on the display 150.

Examples of such image processing functions include gamma correction, interpolation, spatial variation, image effecting, image scaling, auto white balancing (AWB), auto exposure (AE), and autofocusing (AF).

Since the temperature sensor of the electronic device 101 is disposed at a position spaced apart from the first and second cameras 180a, 180b at a predetermined distance, as shown in FIGS. 2 and 3, a gap between an image signal for the portion for measurement output from the image sensor 810 and the portion for measurement where infrared light is radiated from the temperature sensor may be present. Accordingly, the image signal processor 820 may perform a function of correcting the gap caused due to the distance between the first and second cameras 180a, 180b and the temperature sensor. Thus, an image of the portion for measurement where infrared light is actually radiated from the temperature sensor may be displayed on the display 150.

Image signal processor 820 may be implemented in the processor 120, e.g., an application processor, that controls multimedia functions, such as a camera function or multimedia data replay function.

If it is determined that the image is in focus by the above operation, the image signal processor 820 outputs an in-focus image. At this time, the processor 120 may be informed that the image is in focus state. Accordingly, when the user presses a body temperature measurement button while the image is in focus, a result of the body temperature measurement may be displayed. Alternatively, the autofocusing function may be continuously performed even after the image of the object is in focus. In such case, the in-focusing operation may be continuously carried out while the user brings the electronic device 101 closer to or farther away from the portion of the object whose temperature is to be measured, with the electronic device 101 in his hand. Body temperature measurement results may be automatically displayed corresponding to a focus matching time of the in-focus image, even without pressing the body temperature measurement button.

Figure 9:
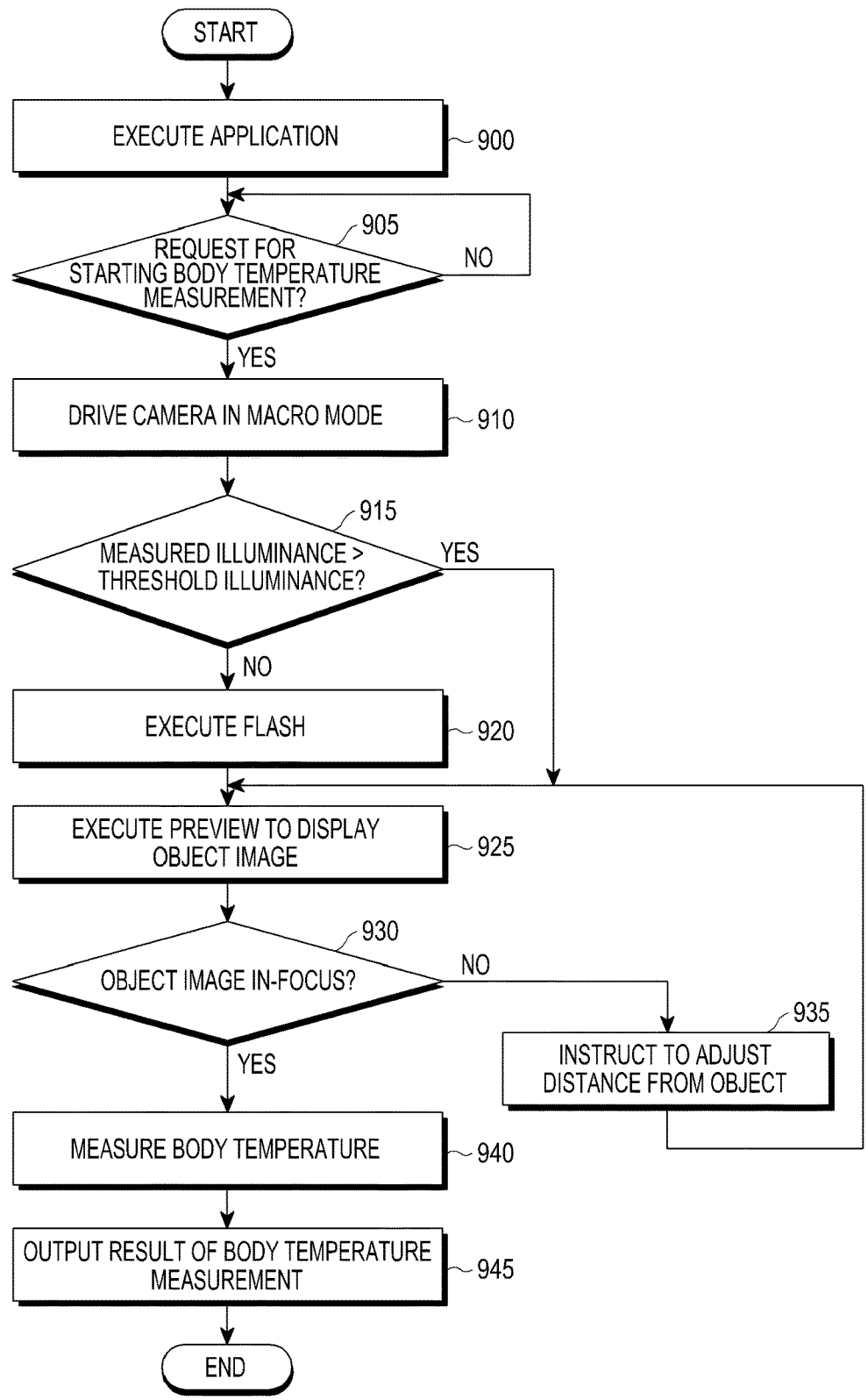
FIG. 9 is a flowchart illustrating a method of body temperature measurement using an electronic device, according to an embodiment of the present invention.

FIG. 9 is a flowchart illustrating a method of body temperature measurement using the electronic device 101, according to an embodiment of the present invention.

Referring to FIG. 9, if an application for body temperature measurement is executed at step 900, it is determined at step 905 whether a user's request for starting body temperature measurement is received. An application for body temperature measurement may be an application that measures the body temperature of a target, displays a result of the measurement, and manages the user's body temperature management information utilizing the result of the body temperature measurement. Further, the application may provide information based on the result of body temperature measurement received from a health-care server 106.

If a request for starting body temperature measurement is received, the electronic device 101 may drive the camera module 180 in macro mode, at step 910. Subsequently, the electronic device 101, at step 915, identifies the ambient light using the illumination sensor to determine whether a measured illuminance is greater than or equal to a threshold illuminance. That is, the electronic device 101 may measure the ambient illuminance and determine whether the amount of light necessary to obtain art image of the object whose temperature is to be measured is greater than or equal to a predetermined amount of light.

If the measured illuminance is less than the threshold illuminance, i.e., in case the amount of light necessary to obtain an image of the object is less than the predetermined amount of light, the electronic device 101, at step 920, executes a flash of the electronic device 101. Then, the electronic device 101, at step 925, obtains an image of the object through the camera module 180 and executes a preview for displaying the image of the object, and at step 930, deter mines whether the image of the object is in focus using the image of the object. That is, the electronic device 101 identifies whether focus matching is achieved. At this time, since the image sensor 810 outputs image signals for the object whose temperature is to be measured on a per-frame basis, an in-focus image is determined from among the output images.

If the image of the object is out of focus, that is, there is no in-focus image of the images continuously output from the image sensor 810, the electronic device 101, at step 935, may instruct the user to adjust the distance from the object whose temperature is to be measured to the electronic device 101. For example, the out-of-focus image of the object may be displayed while simultaneously displaying whether the distance between the portion for measurement of the measured target and the camera reaches the focal distance. Or, the electronic device 101 may induce the user to move to the measured position by outputting an alert sound, an instruction voice, or instruction message.

In contrast, if the image of the object is in focus, a body temperature may be measured at step 940. At this time, the image signal processor 820 of the electronic device 101 determines an in-focus image from among the images and informs the processor 120 of the focus matching time of the image of the object. The processor 120 controls the temperature sensor, e.g., the temperature sensors 170a, 170b, commanding the temperature sensor to measure body temperature. If the distance adjustment is performed to position the electronic device 101 to the focal distance, it may be reported to the user, and body temperature may be then measured. As such, the electronic device 101 allows the user to keep the electronic device 101 stationary by outputting an indication to a user that the electronic device 101 is disposed at the in-focus position, that is, at the position where the body temperature can be measured, through any one of the speaker or a vibration device.

Subsequently, if body temperature is measured, the electronic device 101, at step 945, outputs the result of the body temperature measurement. At this time, the user may measure a body temperature immediately when the in-focus state is achieved, even without pressing a separate button for measurement, while the electronic device 101 is held stationary, at the position where the electronic device 101 is at the focal distance from the portion of the body at which a temperature is to be measured. Thereafter, the result of the body temperature measurement is displayed. Alternatively, the body temperature measurement may be implemented when the user presses a measurement button for viewing the image for the portion of the object whose temperature is to be measured and that is positioned in-focus.

10A is a flowchart illustrating a method of measuring body temperature, according to an embodiment of the present invention.

Figure 10A:
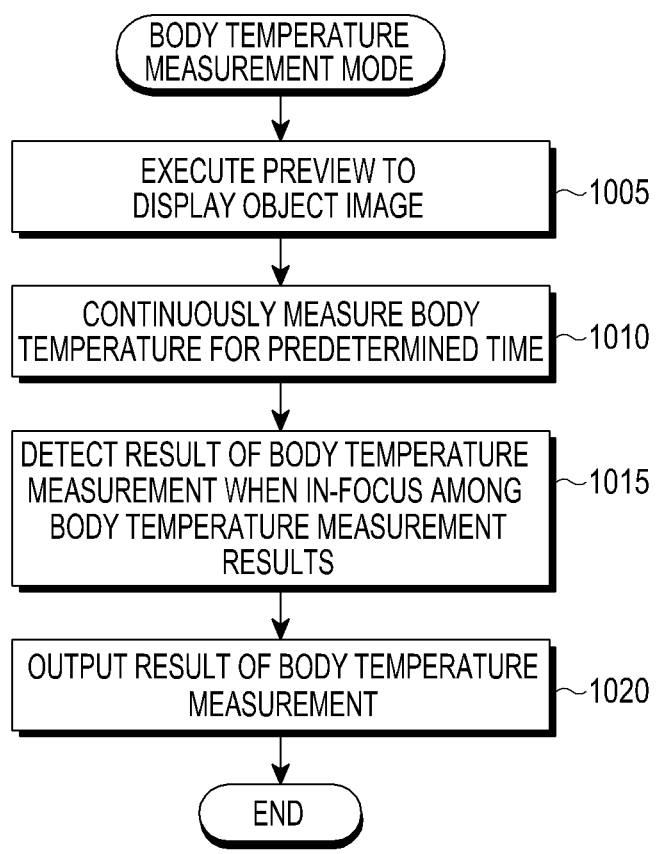
FIG. 10A is a flowchart illustrating a method of measuring body temperature, according to an embodiment of the present invention.

Referring to FIG. 10A, the electronic device 101, in body temperature measurement mode, at step 1005, executes a preview for displaying an image of the object, and at step 1010, continuously measures body temperature for a predetermined time. In other words, the body temperature measurement is continuously performed until an in-focus image of the object whose temperature is to be measured is determined, while previewing images of the object whose temperature is to be measured. Accordingly, when an image of an object is rendered in-focus, the electronic device 101, at step 1015, detects the body temperature measurement result when the image is in-focus, from among body temperature measurement results. Then the electronic device 101, at step 1020, outputs the body temperature measurement result.

Figure 10B:
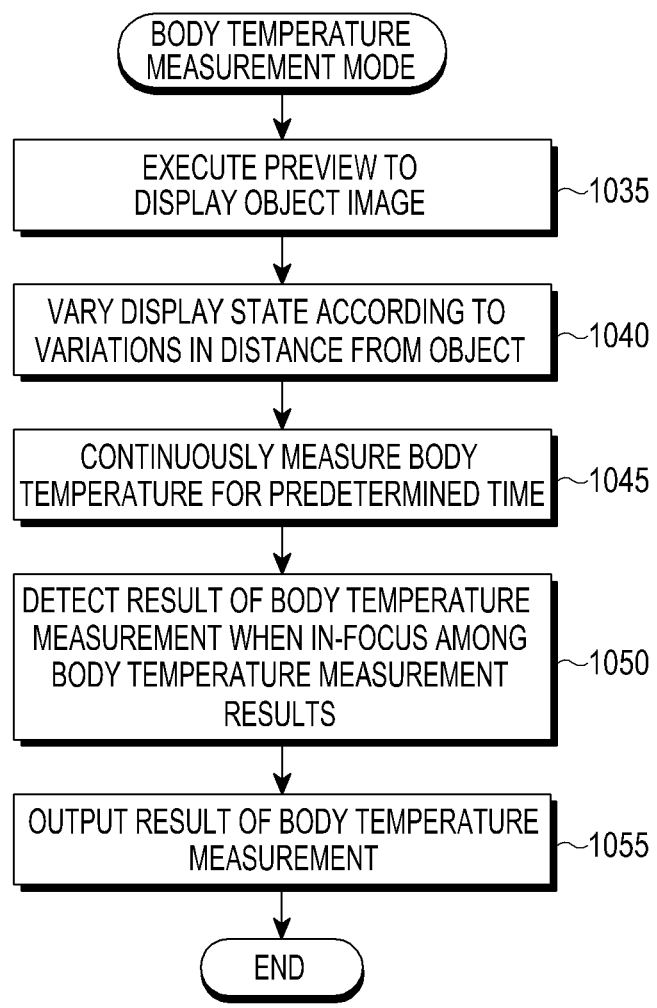
FIG. 10B is a flowchart illustrating a method of measuring body temperature, according to an embodiment of the present invention.

FIG. 10B is a flowchart illustrating a method of measuring body temperature, according to an embodiment of the present invention.

Referring to FIG. 10B, upon switching the body temperature measurement mode, the electronic device 101, at step 1035, executes a preview displaying a preview image. At this time, the user may bring the electronic device 101 closer to or farther away from the portion of the portion of the body at which a temperature is to be measured for focusing, and in such case, the electronic device 101, at step 1040, may vary the state displayed on the display 150 depending on variations in the distance from the portion of the body at which a temperature is to be measured. Steps 1045, 1050, and 1055 correspond to steps 1010, 1015, and 1020 of FIG. 10A, and will not be discussed in further detail.

Figure 11A:
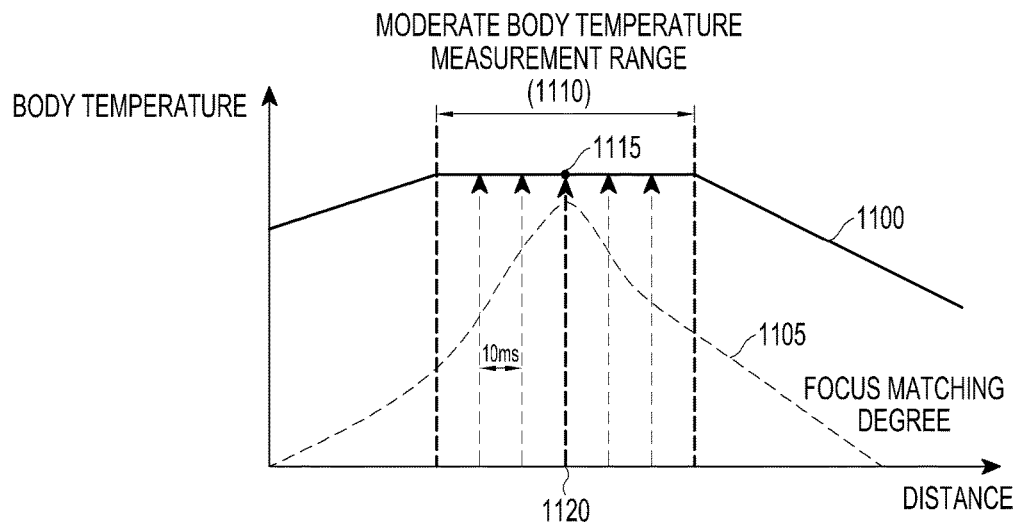
FIGS. 11A and 11B are graphs illustrating a relationship between temperatures corresponding to variations in a measurement distance, according to an embodiment of the present invention.
Figure 11B:
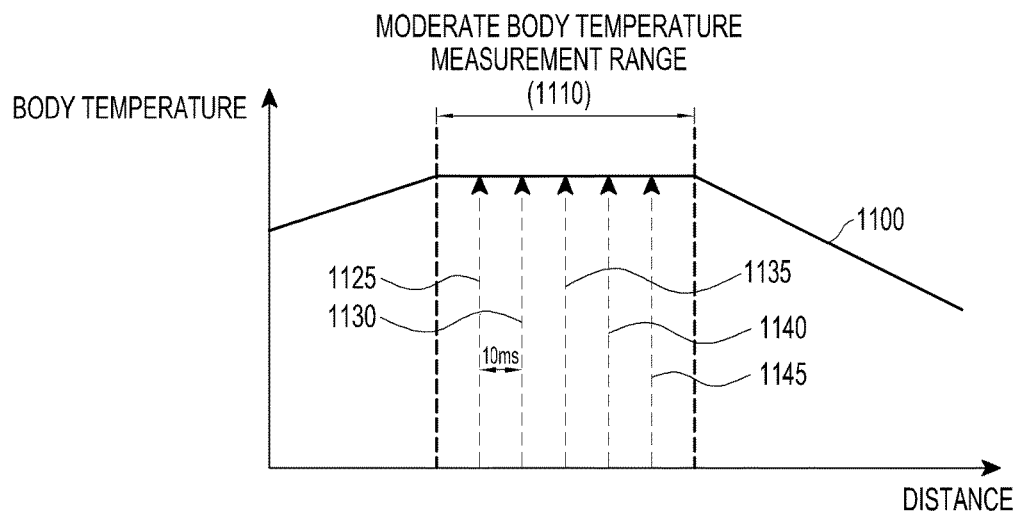

FIGS. 11A and 11B are graphs illustrating a relationship between temperatures corresponding to variations in a measurement distance, according to an embodiment of the present invention.

In FIG. 11A, the temperature variation 1100 and the focus matching degree 1105 are shown depending on variations in the measurement distance, the horizontal axis refers to the distance between the camera, e.g., the first and second cameras 180a, 180b, and the object whose temperature is to be measured, and the vertical axis refers to the temperature of the portion of the object whose temperature is to be measured. As shown in FIG. 11A, as the camera, moves from a moderate range 1110 for body temperature measurement and goes away from the portion of the object whose temperature is to be measured, the body temperature value decreases, and as the camera approaches the portion of the object whose temperature is to be measured, close to the moderate body temperature measurement range 1110, the body temperature value is decreased as well.

Accordingly, measurement of the body temperature in the section where the body temperature is maintained relatively constant depending on the variations in measurement distance reduces errors and deviations between measured values. This section is defined as the moderate body temperature measurement range 1110. Further, the focus matching degree 1105 according to the measurement distance denotes a degree as to how well focusing is done, and the focus matching degree may be acquired through a contrast degree of an image, i.e., a preview image, received through the camera. The contrast scheme refers to a scheme that discovers a position of the lens at which the image is clearly viewed, i.e., the position at which a high contrast ratio is shown, by moving the focus adjustment lens. Such a scheme is a scheme in which, after the lens is moved, the target for focus adjustment, i.e., the object whose temperature is to be measured, is identified for its contrast ration, and the focus adjustment lens is stopped from moving at the position where the highest contrast ratio is obtained, and thus, does not require any distance measuring sensor or other optical parts and provides a high degree of focus adjustment.

Accordingly, the position 1115 with the highest focus matching degree, from among the moderate body temperature measurement range 1110, corresponds to the macro focal distance 1120. In other words, the body temperature 1115 measured in the focal distance 1120 with the highest focus matching degree belongs to the moderate body temperature measurement range 1110. Accordingly, a body temperature measurement is performed using the characteristic that body temperature varies depending on measurement distances.

Accordingly, the user may identify whether the in-focus state is achieved upon each body temperature measurement even without bringing the electronic device 101 in contact with the portion of the object whose temperature is to be measured, and thus, may be aware of what distance has to be left between the camera and the object whose temperature measurement is to be made. As such, since the focal distance corresponds to a distance at which the distance between the camera and the object remains constant, a body temperature measurement may be performed at the position spaced apart at the constant distance, and thus, errors in measurement depending on variations in measurement distance may be reduced, thus leading to enhanced accuracy.

Meanwhile, FIG. 11B is a graph illustrating the body temperature variation 1100 depending on variations in measurement distance. FIG. 11B illustrates an example in which body temperature module is continuously performed for a predetermined time.

Referring to FIG. 11B, the temperature sensor continuously measures body temperature while a focus matching degree is continuously identified using images input through the camera, e.g., the first and second cameras 180a, 180b. As shown in FIG. 11B, the temperature sensor actually performs the measurement at each predetermined sampling period (e.g., available for up to 10 msat 1125, 1130, 1135, 1140, and 1145) when performing continuous body temperature measurement.

Any one of the temperatures 1125, 1130, 1135, 1140, and 1145 continuously measured is determined as the final temperature for the object. The temperature 1135 measured at the time of focus matching is determined as the final temperature for the object.

Figures 12A, 12B, 12C:
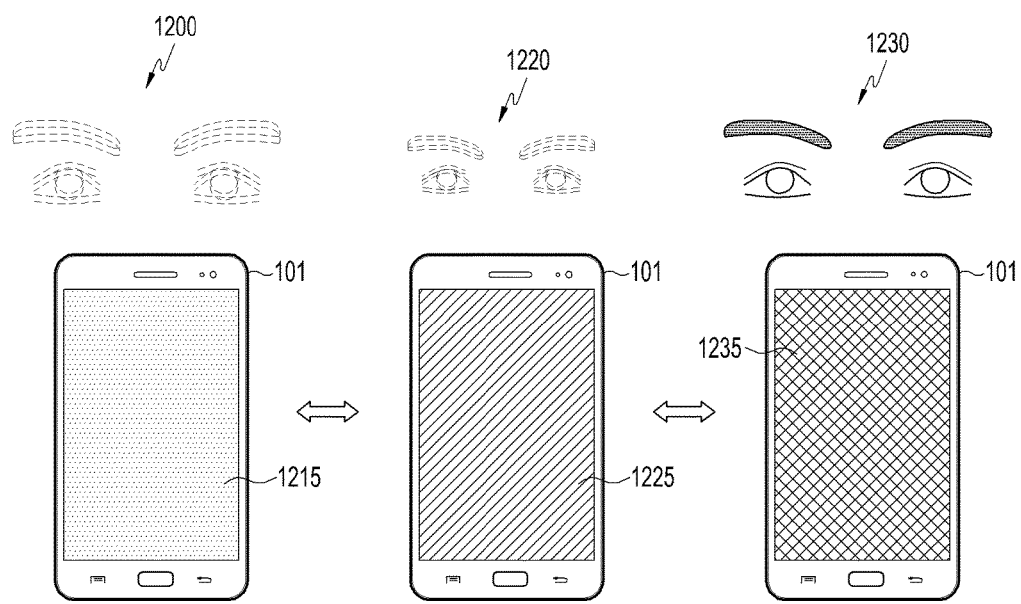
FIGS. 12A-12C are diagrams illustrating an example of display screens corresponding to variations in measurement distance, according to an embodiment of the present invention.

FIGS. 12A-12C are diagrams illustrating an example of display screens corresponding to variations in measurement distance, according to an embodiment of the present invention. As shown in FIGS. 12A-12C, an image including at least one color may be displayed on the screen of the electronic device 101.

For example, as shown in FIG. 12A, for an image 1200 that is out of focus, as the object is too close in distance to the camera, a first color screen 1215 is displayed on the electronic device 101. For an image 1220 that is out of focus, as the distance between the object and the camera departs from the focal distance, a second color screen 1225 is displayed on the electronic device 101. For an image 1230 with the distance between the object and the camera, corresponding to the focal distance, as third color screen 1235 may be displayed on the electronic device 101. As such, as a color-changing image is displayed on the screen of the electronic device 101, the user may identify whether body temperature measurement is possible at the position.

Figure 13:
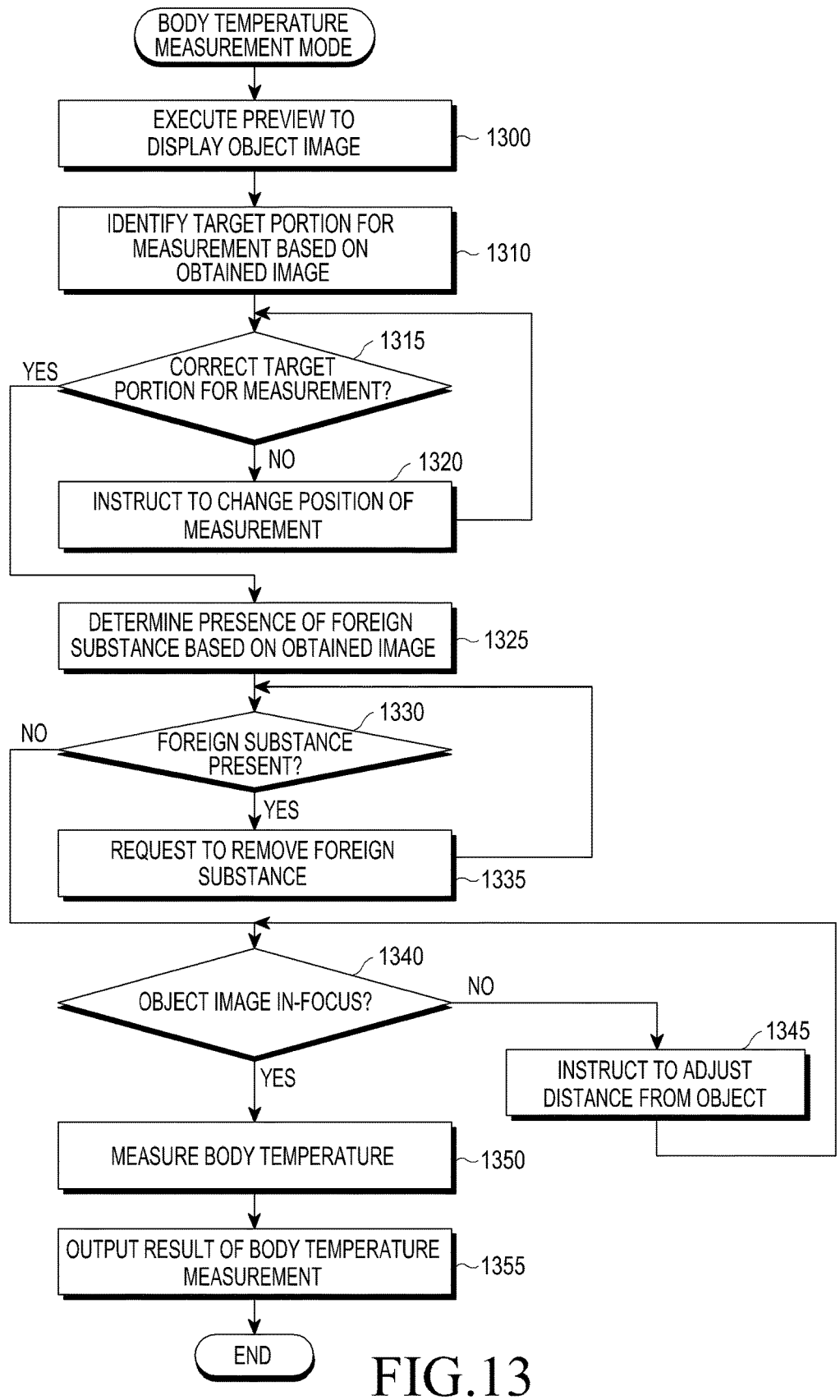
FIG. 13 is a flowchart illustrating a method of measuring body temperature, according to an embodiment of the present invention.

FIG. 13 is a flowchart illustrating a method of measuring body temperature, according to an embodiment of the present invention.

Referring to FIG. 13, the electronic device 101, at step 1300, obtains an image of the object and executes a preview for displaying the image of the object. Subsequently, the electronic device 101, at step 1310, identifies a target portion for measurement based on the obtained image. For example, if the target portion for measurement is the central forehead, the image of the object being previewed may contain at least part of the eyebrow shape.

It may be determined whether the image of the object includes at least part of the eyebrow shape.

It may be determined whether the image of the object includes at least part of the ear shape.

The target portion for measurement may be identified using the eyebrow shape or ear shape stored in the memory 130 for an object whose temperature was previously measured. Adjustment of the position of measurement may be instructed based on the eyebrow-shaped image previously stored, so that body temperature measurement may be performed at the temporal artery between the eyebrows upon each measurement, thus leading to enhanced measurement accuracy. Further, whether the target portion for measurement corresponds to the forehead including the eyebrow-shaped image may be determined through a facial recognition algorithm, and in the case of the forehead image including the eyebrow-shaped image, adjustment of the position of measurement may be instructed. The guide line along which the eyebrow is positioned, together with the image of the object, may be displayed on the screen, allowing the user to adjust the position of measurement while identifying the target portion for measurement.

The electronic device 101, at step 1315, determines whether the portion is the target portion for measurement, and if yes, proceeds with step 1325, while if no proceeding with step 1320 to instruct to change the position of measurement At step 1325, it is determined, based on the obtained image, whether there are foreign substances, such as hairs or sweat. If it is determined at step 1330 that there are foreign substances on the lens of the camera or on the portion of the body at which a temperature is to be measured, removal of the foreign substances may be requested at step 1335. In contrast, if it is determined that there are no foreign substances, it is determined whether the image of the object is in focus at step 1340.

It may be determined if there are foreign substances while the user himself views the screen, and the foreign substances may be removed. It may be determined if there are foreign substances using an RGB color recognition function of the electronic device 101, for example, using the differences between black hair and skin color. If it is determined that there are foreign substances, the electronic device 101 may be used to report this to the user to request to removal of the foreign substances. Although the example in which the RGB color recognition function is used to determine whether there are foreign substances has been described above, algorithms for determining the presence or absence of foreign substances are not limited thereto.

Although the forehead has been used as the portion of the object whose temperature is to be measured, above in connection with FIGS. 12A-12C, the method may apply likewise to the portion behind an ear lobe, where the temporal artery passes. For example, whether the position is the target portion for measurement may be determined using an ear-shaped image previously stored, and if the determination as to whether there are foreign substance shows that hairs are present, it may be requested to pull all the hair back behind the ears. As such, once an image is output using the camera on the portion where the temporal artery is distributed, body temperature measurement is possible as well.

If the image of the object is out of focus, that is, in case none of the images continuously input are in-focus, the electronic device 101, at step 1345, instructs the user to adjust the distance from the object whose temperature is to be measured. In contrast, in case the image of the object is in focus, body temperature may be measured at step 1350, and a result of the body temperature measurement may be output at step 1355.

Meanwhile, there may be provided a fraction of visually displaying the state of execution in body temperature measurement mode. For example, when the body temperature measurement mode is in execution, the body temperature measurement execution state may be displayed on the display 150.

Figures 14A, 14B:
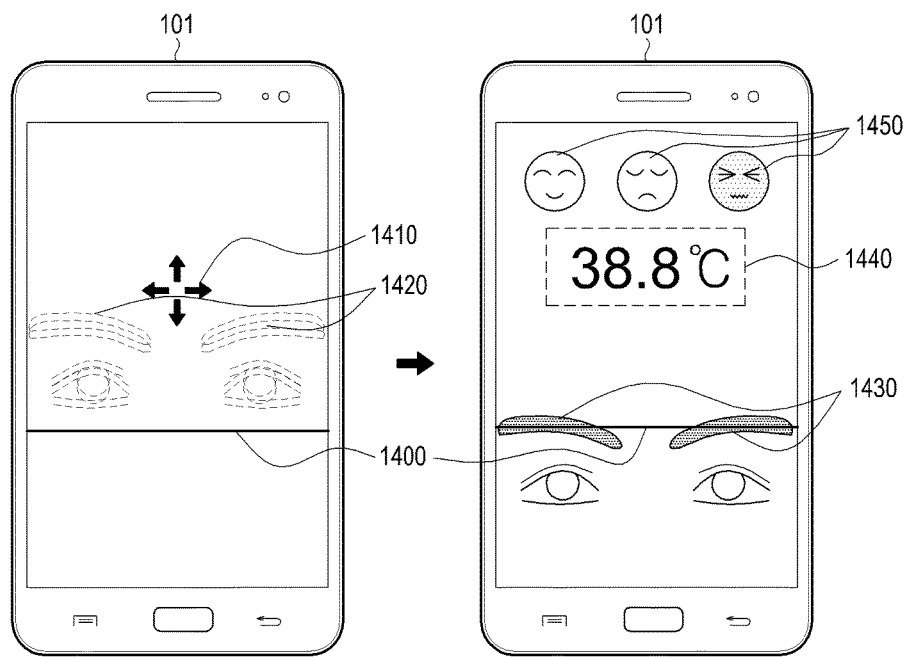
FIGS. 14A and 14B are diagrams illustrating an example of screens of an electronic device when a body temperature measurement is taken, according to an embodiment of the present invention.

FIGS. 14A and 14B are diagrams illustrating an example of screens of an electronic device when a body temperature measurement is taken, according to an embodiment of the present invention. First, FIG. 14A illustrates an out-of-focus image 1420 and an indicator 1410 and guide line 1400 for adjusting the position of measurement.

As shown in FIG. 14A, if the portion of a body at which a temperature is to be measured is out-of-focus, an image of the portion of the body including an eyebrow, which is out-of-focus, may be displayed. Further, since a body temperature measurement should be performed on the central forehead, the indicator 1410 for adjusting the position of measurement may be displayed. Although FIG. 14A illustrates an example where the information for inducing the position of measurement to be adjusted is displayed in the form of the directional indicator 1410 or guide line 1400, the inducing information may be displayed in other various forms such as an instruction message or a "+"-shaped icon. Further, the guide line 1400 may be displayed. For example, the user may adjust the position of measurement so that the eyebrow is positioned on the guide line 1400, viewing the guide line 1400.

FIG. 14B illustrates a resultant screen for body temperature measurement after adjusting the position of measurement. FIG. 14B illustrates an example of an in-focus image, with the position of measurement adjusted so that the eyebrow 1430 fits the guide line 1400. As such, if the in-focus state is achieved, a result of body temperature measurement may be displayed. As shown in FIG. 14B, the in-focus image, the measured body temperature value 1440, and a screen configured based on the measured body temperature value may be displayed. Alternatively, if the body temperature measurement is complete after the in-focus image has been displayed, a screen configured based on the measured body temperature value may be displayed.

Such body temperature measurement results may be displayed on the screen through various indicators 1450. For example, the indicators may be represented in various forms, such as a character indicating "normal" or an indicator indicating a warning.

Further, if, upon measuring the body temperature, the measurement state is not performed correctly, an indicator may be displayed on the screen to indicate the same. For example, if the user tries to measure the body temperature, with the electronic device 101 placed at a wrong position, the electronic device 101 may provide the user with instruction information for the user to relocate the electronic device 101 to a right position for measurement, e.g., a position where an artery blood vessel passes between the user's eyebrows to measure the body temperature. Such instruction information may be offered to the user through at least one of a vibration, an image, and a voice.

Figure 15A:
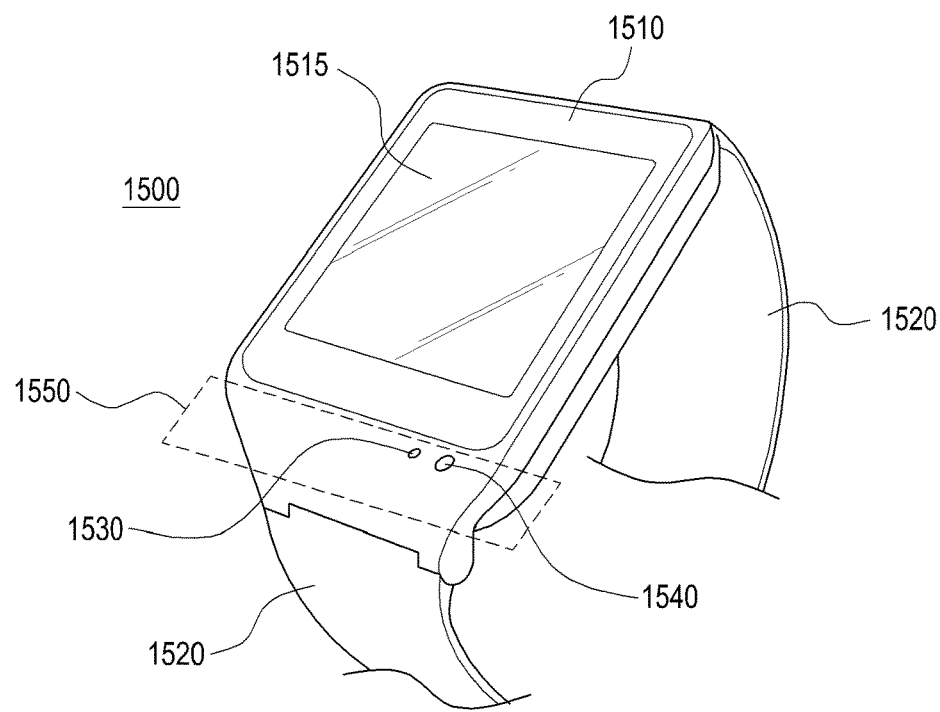
FIGS. 15A and 15B are perspective views illustrating watch-type wearable electronic devices, according to an embodiment of the present invention.
Figure 15B:
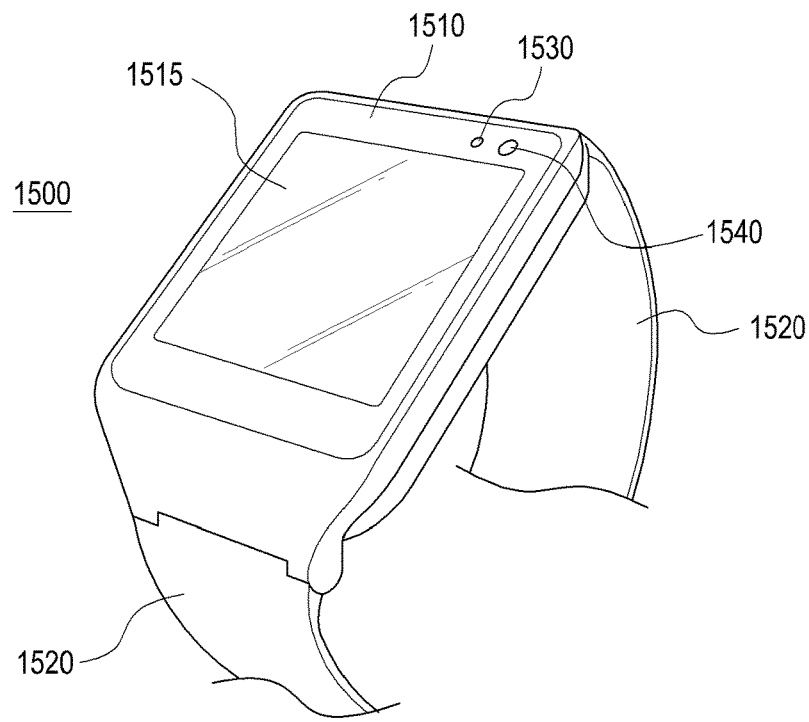

FIGS. 15A and 15B are perspective views illustrating watch-type wearable electronic devices, according to an embodiment of the present invention.

Referring to FIG. 15A, a wearable electronic device 1500, e.g., an electronic device 101 that may be put on the user's wrist, such as a wristwatch or bracelet, is illustrated. The wearable electronic device 1500 includes a body portion 1510 and a strap portion 1520.

Various embodiments of the present invention are not limited thereto, and according to embodiments of the present invention, the electronic device 101 may be implemented as various communication devices or assistant medical devices. Further, the electronic device 101 may apply to a curved part of the user's body in a diversified manner. The curved part of the user's body may be, e.g., a wrist, elbow, or ankle. The electronic device 101 may be easily put on various parts of the user's body depending on the configuration of a wearing unit.

As such, the wearable device 1500 may be collectively referred to as any electronic device that may be worn on the user's wrist, including, but not limited to, a typical type of analog or digital wristwatch, a smartwatch, and a bio information measuring device. The body portion 1510 of the wearable electronic device 1500 may be a watch module of the analog or digital watch or a module equipped with a display and various multimedia functions, and may include a module for sensing a bin signal. Further, the body portion 1510 of the wearable electronic device 1500 includes a display 1515, and the display 1515 may be integrated with a touch panel and may be utilized as an input device.

At least one of the camera module 180 and the temperature sensor, e.g., temperature sensors 170a, 170b, may be disposed on the bezel 1550 surrounding the display 1515 of the wearable electronic device 1500. FIG. 15A illustrates an example in which a camera module 1530 and a temperature sensor 1540 are disposed at a lower end on the front surface of the body portion 1510. In contrast, FIG. 15B illustrates an example in which a camera module 1530 and a temperature sensor 1540 are disposed at an upper end on the front surface of the body portion 1510. Various changes or modification may be made to the arrangement and/or position as long as at least one of the camera module 1530 and the temperature sensor 1540 are coupled with the body portion 1510 to be able to receive an image for the object whose temperature is to be measured or measure the temperature of the object.

Figure 16:
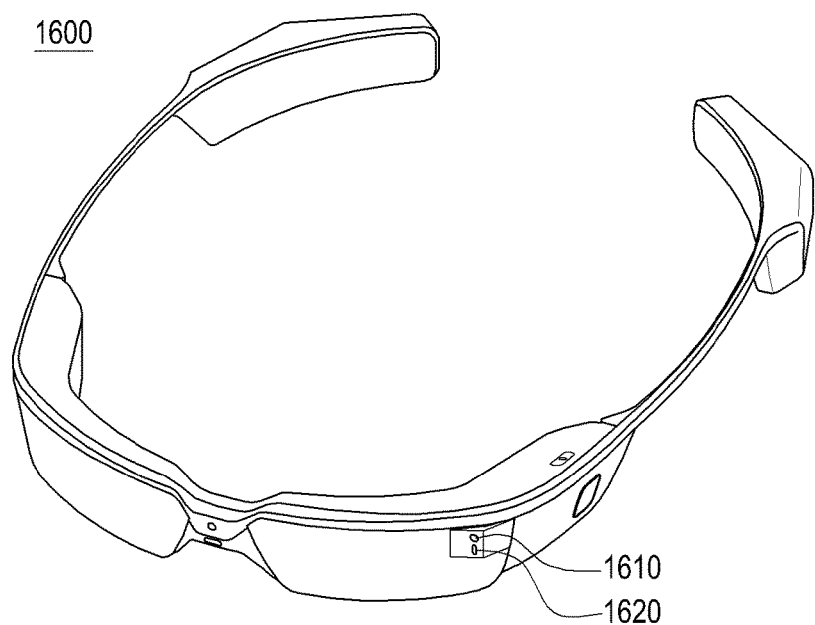
FIG. 16 is a perspective view illustrating an electronic device embodied in the form of a pair of glasses, according to an embodiment of the present invention.

FIG. 16 is a perspective view illustrating an electronic device 1600 embodied in the form of a pair of glasses, according to an embodiment of the present invention.

Referring to FIG. 16, the electronic device 1600 may be implemented as a display device wearable on the user's body, e.g., face or head. A see-through display unit may be positioned in a region adjacent to the user's head (e.g., an eye), and a speaker may be positioned in a region adjacent to the users ear to provide the user with visual information and auditory information. The electronic device 1600 may include a glasses-type display device or a helmet-type display device. The electronic device 1600 may also include a monocular-type display device with a single display unit for displaying content or a. binocular-type display unit with a plurality of display units.

A temperature sensor 1610 and a camera module 1620 may be disposed adjacent to each other at portions on the front surface of the see-through display unit. The distance between the temperature sensor 1610 and the camera module 1620 may be varied depending on the performance or structure of the electronic device 1600.

Figure 17:
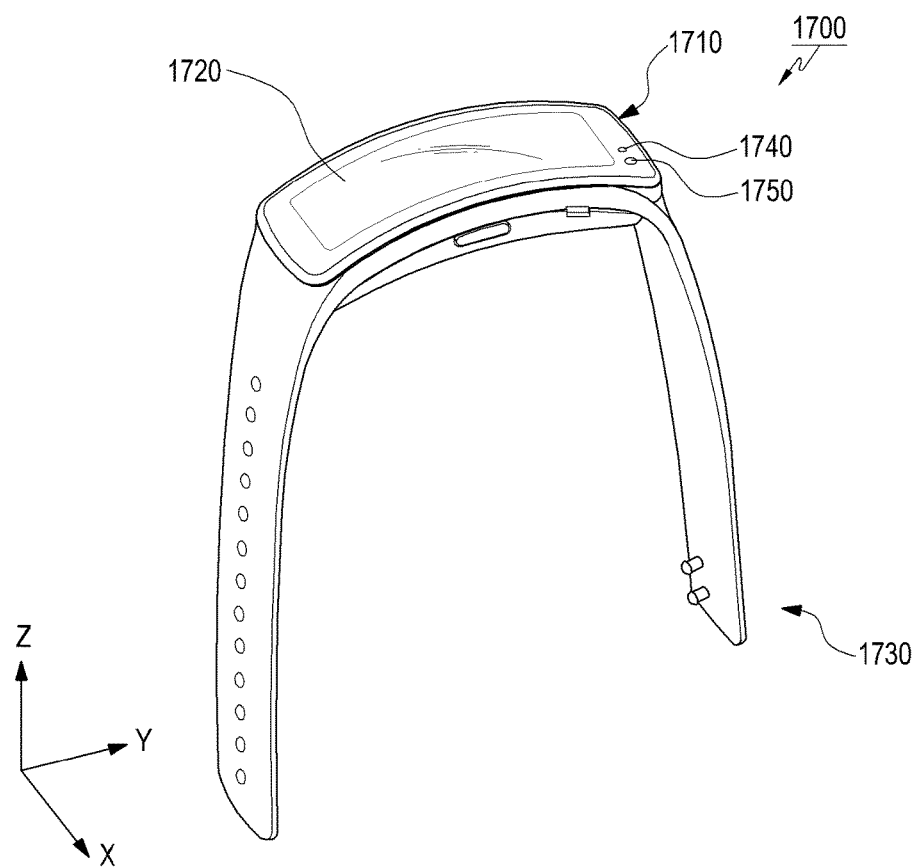
FIG. 17 is a perspective view illustrating a band-type wearable electronic device, according to an embodiment of the present invention.

FIG. 17 is a perspective view illustrating a band-type wearable electronic device 1700, according to an embodiment of the present invention.

Referring to FIG. 17, a body portion 1710 of the wearable electronic device 1700 may include a front surface and a rear surface contacting the user's body when the wearable electronic device 1700 is put on the user. A display 1720 is disposed on the front surface of the body portion 1710 and a temperature sensor 1750 is disposed at a position adjacent to the display 1720 to measure a bio signal from the user, e.g., the user's body temperature. Further, a camera module 1740 may be disposed at a position adjacent to the temperature sensor 1750 In this case, the display 1720 is disposed on the front surface of the body portion 1710. The body temperature measurement screen displayed is easily viewed by a user. The camera module 1740 and/or the temperature sensor 1750 can be disposed on the front surface. Accordingly, the body portion 1710 may be shaped to tightly contact the user's wrist.

As described above, a temperature sensor and a camera module may be mounted in various types of electronic devices, and the distance between the temperature sensor and the camera module may be varied depending on the performance or structure of the electronic device. Although the temperature sensor and the camera module are shown disposed adjacent to each other in each of the electronic devices that have been described in connection with FIGS. 15A-17, one of the temperature sensor and the camera module may be provided at different locations in each of the electronic devices. Further, since body temperature measurement should be able to be performed even during the nighttime or in a space with no illumination from the user's perspective, each electronic device may further include a flash for illuminating the object whose temperature is to be measured and an illumination sensor for detecting the amount of ambient light.

Figure 18A:
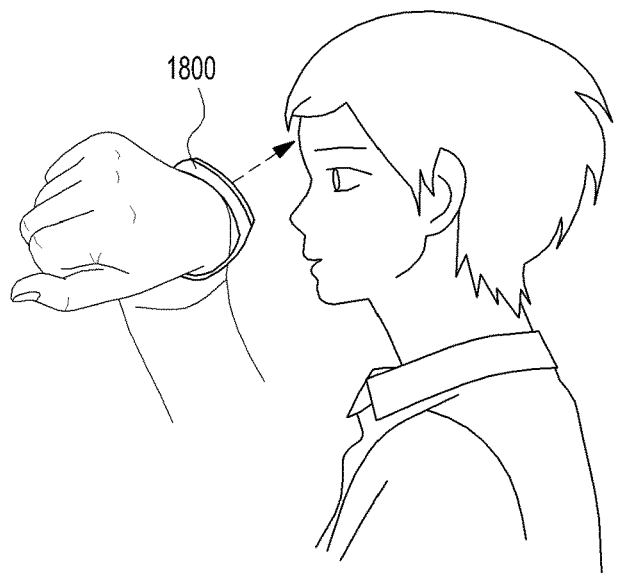
FIGS. 18A and 18B are diagrams illustrating an example of a body temperature measurement method using a wearable electronic device, according to an embodiment of the present invention.
Figure 18B:
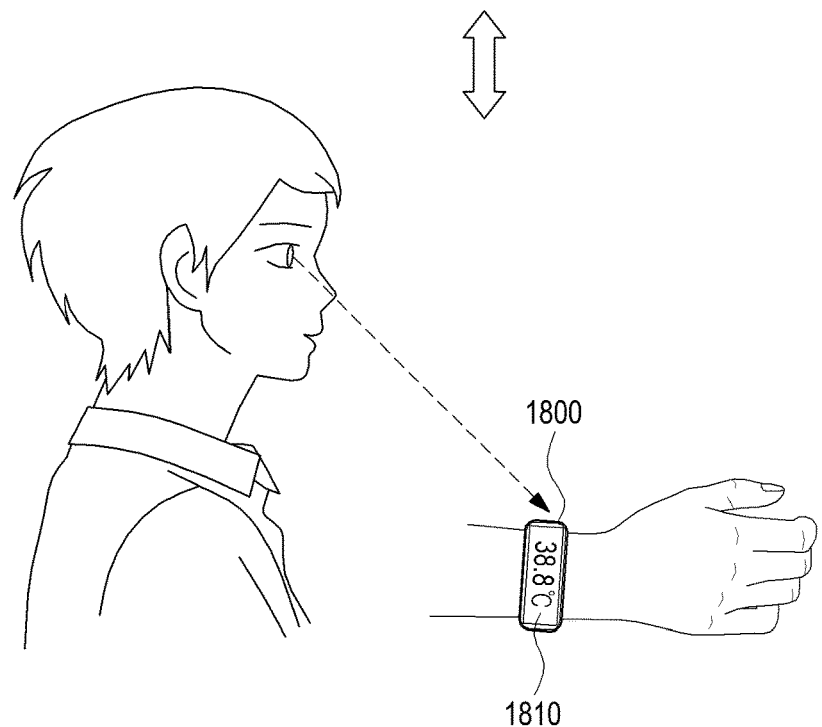

FIGS. 18A and 18B are diagrams illustrating an example of a body temperature measurement method using a wearable electronic device, according to an embodiment of the present invention.

FIG. 18A illustrates an example of the operation in which the user wearing the wearable electronic device 1800 on his wrist brings the wearable electronic device 1800 close to his forehead and then measures his body temperature with the wearable electronic device 1800 not contacting the forehead. Even when the wearable electronic device 1800 has a display 1810 (FIG. 18B), the user may have difficulty measuring his body temperature while viewing the display 1810. Accordingly, the user may be signaled with an alert sound, instruction voice, or haptic effect provided by the electronic device 1800 so that the user may easily identify the distance between the wearable electronic device 1800 and the portion of the object whose temperature is to be measure. Further, the inclusion of foreign substances such as sweat or hairs that may be present on the portion of the object whose temperature is to be measured may be reported through an alert sound, instruction voice, or haptic effect.

Further, if the body temperature measurement is complete, an alert sound, instruction voice, or haptic effect indicating that the body temperature measurement is complete may be output by the electronic device 1800, and a screen with the result of the body temperature measurement may be displayed at a position where the user descends his hand to view the display 1810, allowing the user to identify the result of the body temperature measurement (FIG. 18B).

FIGS. 19A-20D are diagrams illustrating examples of body temperature measurement methods using different electronic devices, according to an embodiment of the present invention.

Figures 19A, 19B, 19C, 19D:
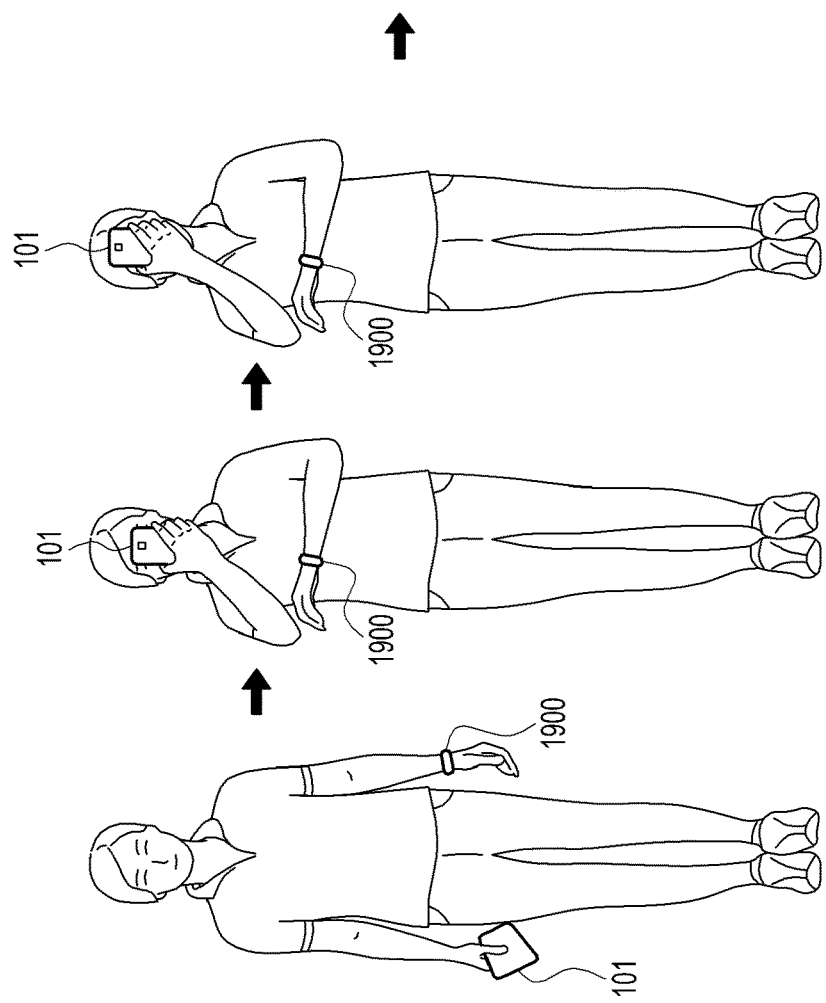

First, as shown in FIG. 19A, the user is wearing a wearable electronic device 1900 on his wrist while holding an electronic device 101, e.g., a smartphone, in his hand. The user brings the electronic device 101 close to his forehead to measure his body temperature, adjusting the distance from the forehead, i.e., the focal distance, as shown in FIGS. 19B and 19C. The user may then view the result of the body temperature measurement through the screen displayed on the display of the wearable electronic device 1900 as shown in FIG. 19D. In this case, the electronic device 101 has both a temperature sensor and a camera module and remains linked with the wearable electronic device 1900 through a short-range communication protocol, e.g., Bluetooth® protocol.

Since the wearable electronic device 1900 is linked with the electronic device 101, the electronic device 101 may transmit the result of the body temperature measurement to the wearable electronic device 1900. Alternatively, the electronic device 101 may transmit all or some of images input in real-time to the wearable electronic device 1900, displaying a preview image for body temperature measurement. Alternatively, while the body temperature measurement is being conducted, the user may identify whether there is interference due to, e.g., foreign substances, between the temperature sensor and the portion of the object whose temperature is to be measured. The user may view the user's portion of the object whose temperature is to be measured on the display of the wearable electronic device 1900 while keeping the electronic device 101 away from the forehead at a predetermined distance 1910 in order to measure the temperature of the forehead using the electronic device 101. In other words, before measurement is actually perforated, the user may verify information on his body temperature measurement posture or position of measurement through the screen displayed on the display of the wearable electronic device 1900.

Figure 20D:
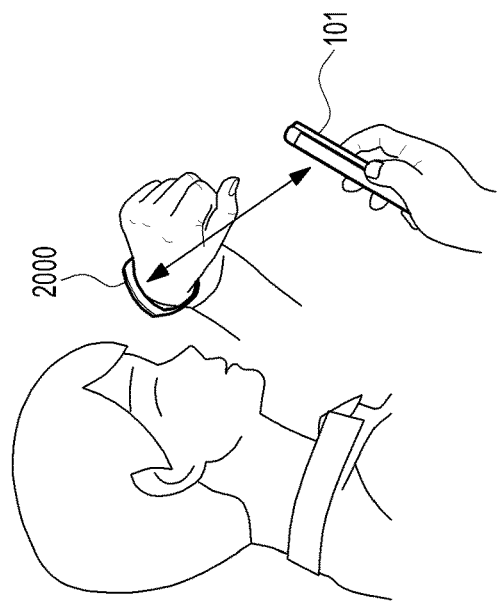
Figure 20C:
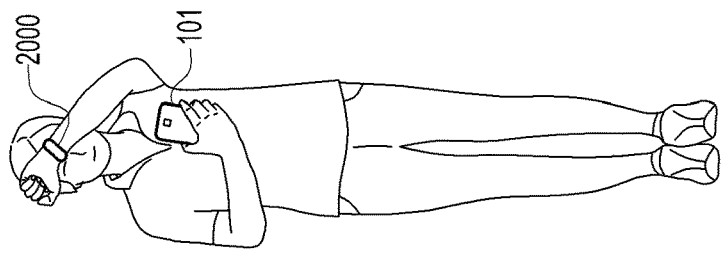
Figure 20B:
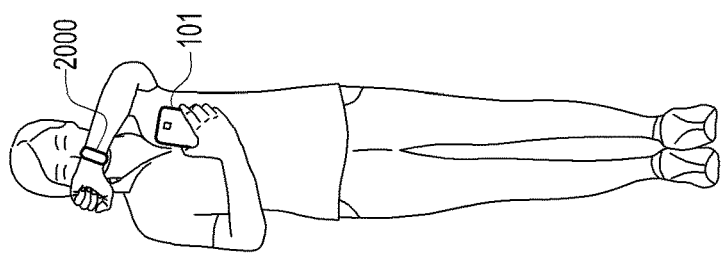
Figure 20A:
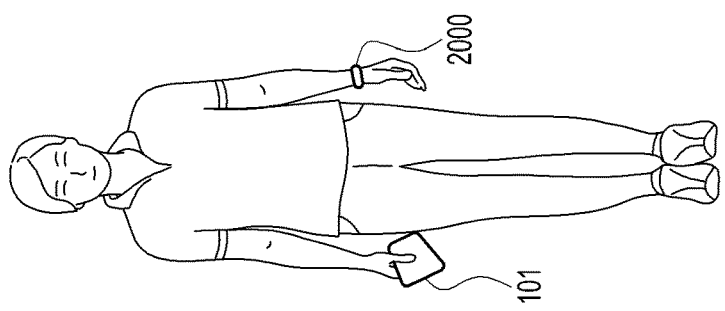
Figure 21:
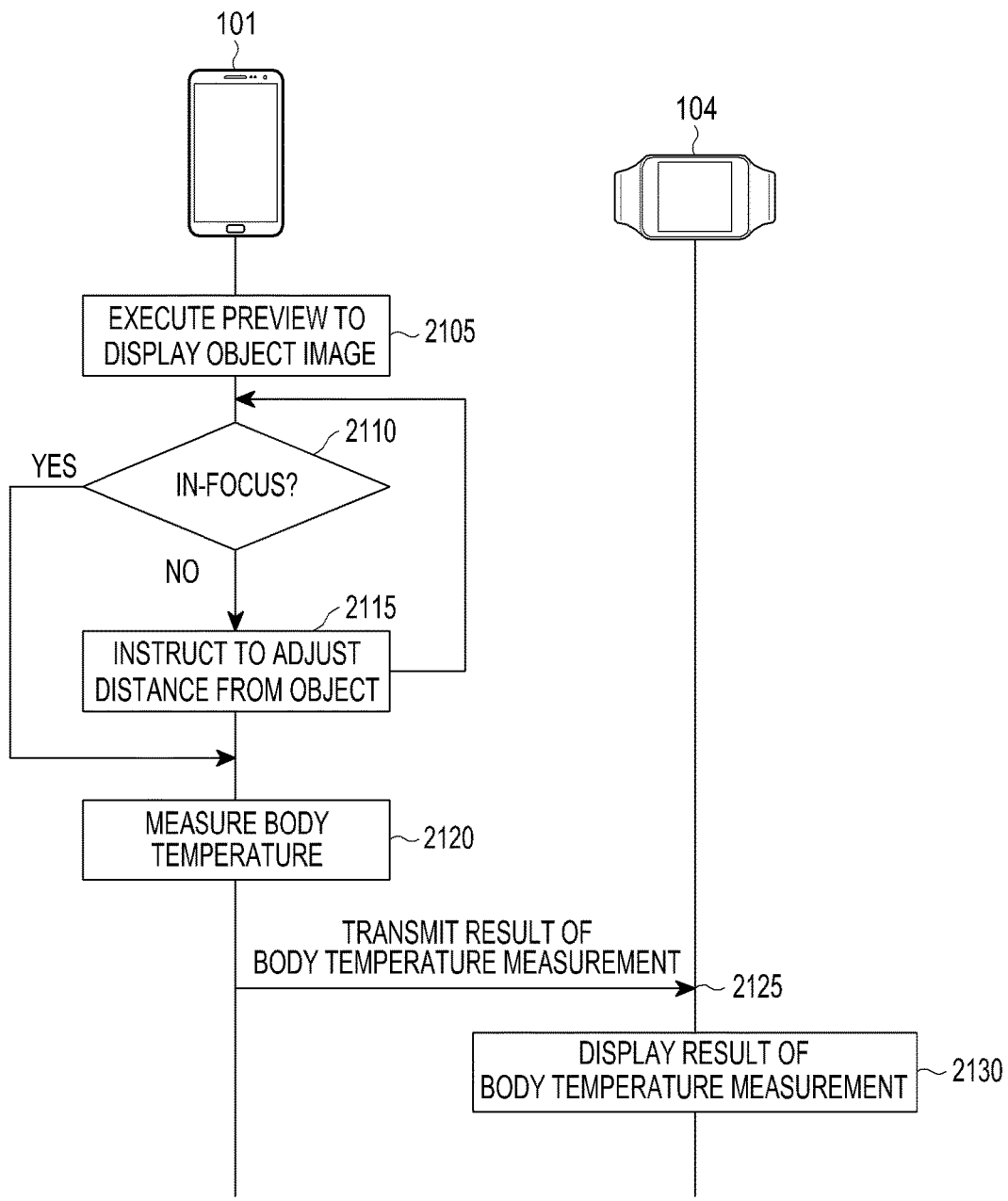
FIG. 21 is a flowchart illustrating a method of measuring body temperature, according to an embodiment of the present invention.

Meanwhile, as shown in FIG. 20A, the user is wearing a wearable electronic device 2000 on his wrist while holding an electronic device 101, e.g., a smartphone, in his other hand. The user brings the electronic device 2000 close to his forehead, adjusting the distance from the forehead, as shown in FIGS. 20B and 20C. The wearable electronic device 2000 has both a temperature sensor and a camera module and remains linked with the electronic device 101 through a short-range communication protocol. The user may measure his body temperature through the wearable electronic device 2000 and may identify the result of the body temperature measurement through the screen displayed on the display of the electronic device 101. As such, since the screen displayed on the display of the electronic device 101 is larger than that of the wearable electronic device 2000, the screen may be configured with various types of information based on the result of the body temperature measurement. FIG. 21 is a flowchart illustrating a method of measuring body temperature, according to an embodiment of the present invention. In this case, the electronic device 101 has both a temperature sensor and a camera module and remains linked with the wearable electronic device 104 through a short-range communication protocol.

Referring to FIG. 21, the electronic device 101, upon receiving a body temperature measurement request, drives the camera module in macro mode. The user may view a preview image for the portion of the object whose temperature is to be measured by bringing the electronic device 101 close to the portion of the object or in a proximity position. Accordingly, when images are obtained on a per-frame basis at step 2105, an in-focus image from among the obtained images may be determined. If it is determined that an image is in-focus at step 2110, body temperature measurement may be performed at the time of that image becoming in-focus at step 2120.

In contrast, if an image is out-of-focus, the user may be instructed to adjust the distance from the object whose temperature is to be measured at step 2115. For example, information inducing the user to bring the electronic device 101 from the position of measurement to the position corresponding to the focal distance may be output through a voice, alert sound, vibration device, or haptic effect, in response to the adjustment of the distance from the object whose temperature is to be measured, the method returns to step 2110 to repeat the above-described operations.

Upon obtaining an in-focus image, the electronic device 101, after measuring body temperature at step 2125, transmits the result of the body temperature measurement to an electronic device 104. Then, the electronic device 104, at step 2130, displays the body temperature measurement result.

Although the body temperature measurement process has been described in terms of transmitting the result of the body temperature measurement to an electronic device 104, the process may apply likewise between the electronic device 101 and the health-care server 106. For example, the electronic device 101 may transmit a measured body temperature value to the health-care server 106, and the health-care server 106 may provide the electronic device 101 with a measurement result based on the measured body temperature value. Such body temperature management may be implemented in a real-time monitored manner, and the electronic device 101 analyzes, processes, and/or treats bio information of the measured target, e.g., a result of monitoring the body temperature in real-time, and outputs the result while simultaneously transmitting the result to the health-care server 106, thereby allowing a result of diagnosis or prescription according to the result to be output.

Figure 22:
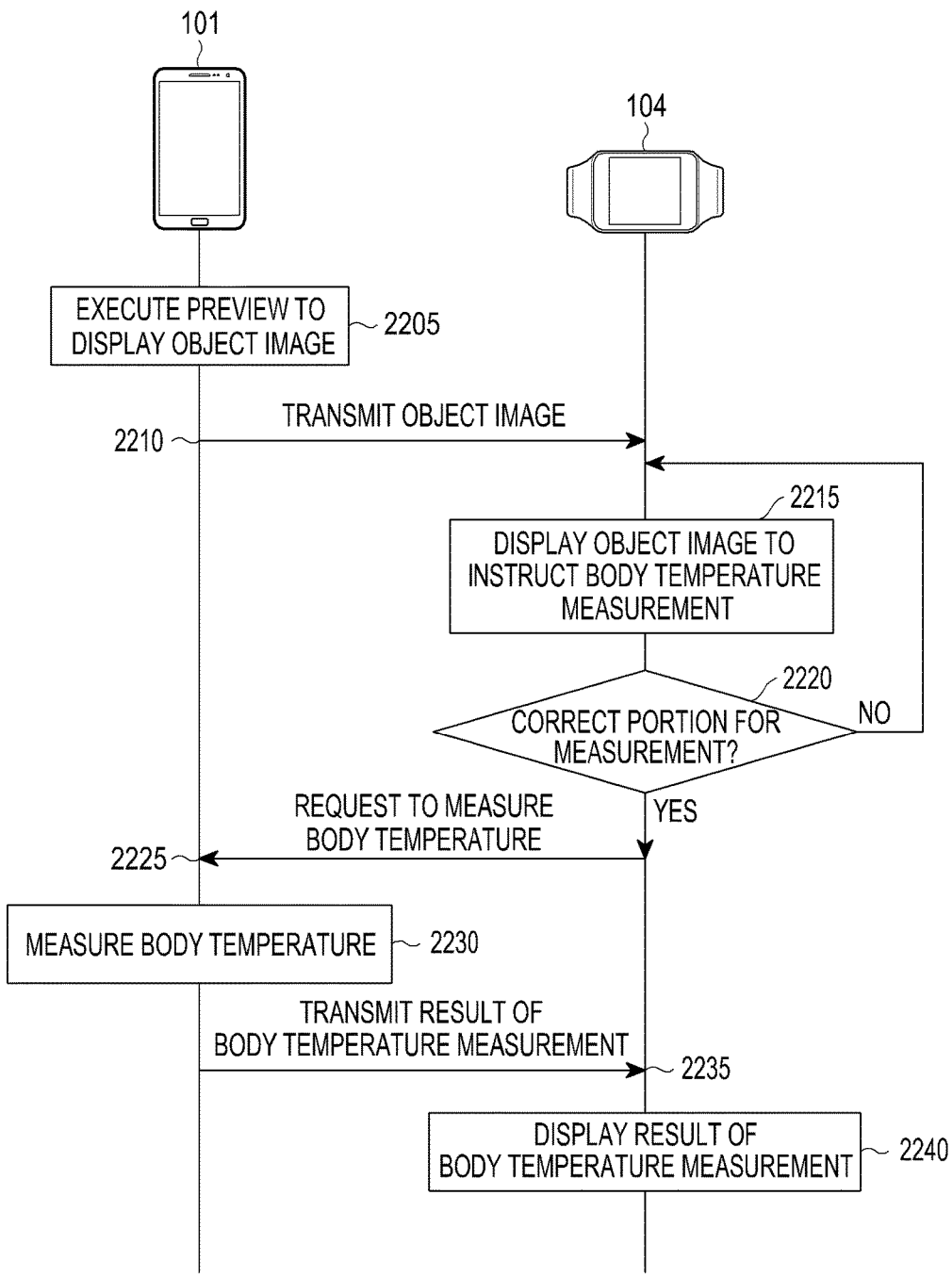
FIG. 22 is a flowchart illustrating a method of measuring body temperature, according to an embodiment of the present invention.

FIG. 22 is a flowchart illustrating a method of measuring body temperature, according to an embodiment of the present invention.

Referring to FIG. 22, if the application for body temperature measurement is executed, the electronic device 101 drives the camera and obtains images on a per-frame basis at step 2205. Subsequently, the electronic device 101, at step 2210, transmits the images input through the camera to the electronic device 104. At this time, all of the images, i.e., the image frames, may be transmitted in real-time, or alternatively, only some of the images may be transmitted, e.g., at predetermined intervals. The electronic device 104, at step 2215, displays the images and instructs the temperature sensor to measure body temperature. The user identifies whether there are foreign substances as well as identifies the portion of the body at which a temperature is to be measured.

Subsequently, the electronic device 104, at step 2220, identifies whether the portion is the portion for measurement, and if yes, proceeds with step 2225 to request the electronic device 101 to measure body temperature. In response to the body temperature measurement request, the electronic device 101, at step 2230, measures body temperature, and at step 2235, transmits the result of the body temperature measurement The electronic device 104, at step 2240, displays the body temperature measurement result.

Although an example in which the electronic device 101, a smartphone, obtains the image for the portion of the object whose temperature is to be measured and measures body temperature has been described above, the process described above in connection with FIG. 22 may apply to where a wearable electronic device obtains images and a smartphone-type electronic device displays the preview image.

For example, an image of the portion of a body at which a temperature is to be measured when the user brings the wearable electronic device on his wrist close to the portion of the body may be displayed on the screen of the smartphone-type electronic device. The user measures body temperature through the wearable electronic device and identifies the result of the body temperature measurement through the screen displayed on the display of the smartphone-type electronic device. As such, use of different types of electronic devices can facilitate measuring body temperature and identifying the result of the body temperature measurement.

Figure 23:
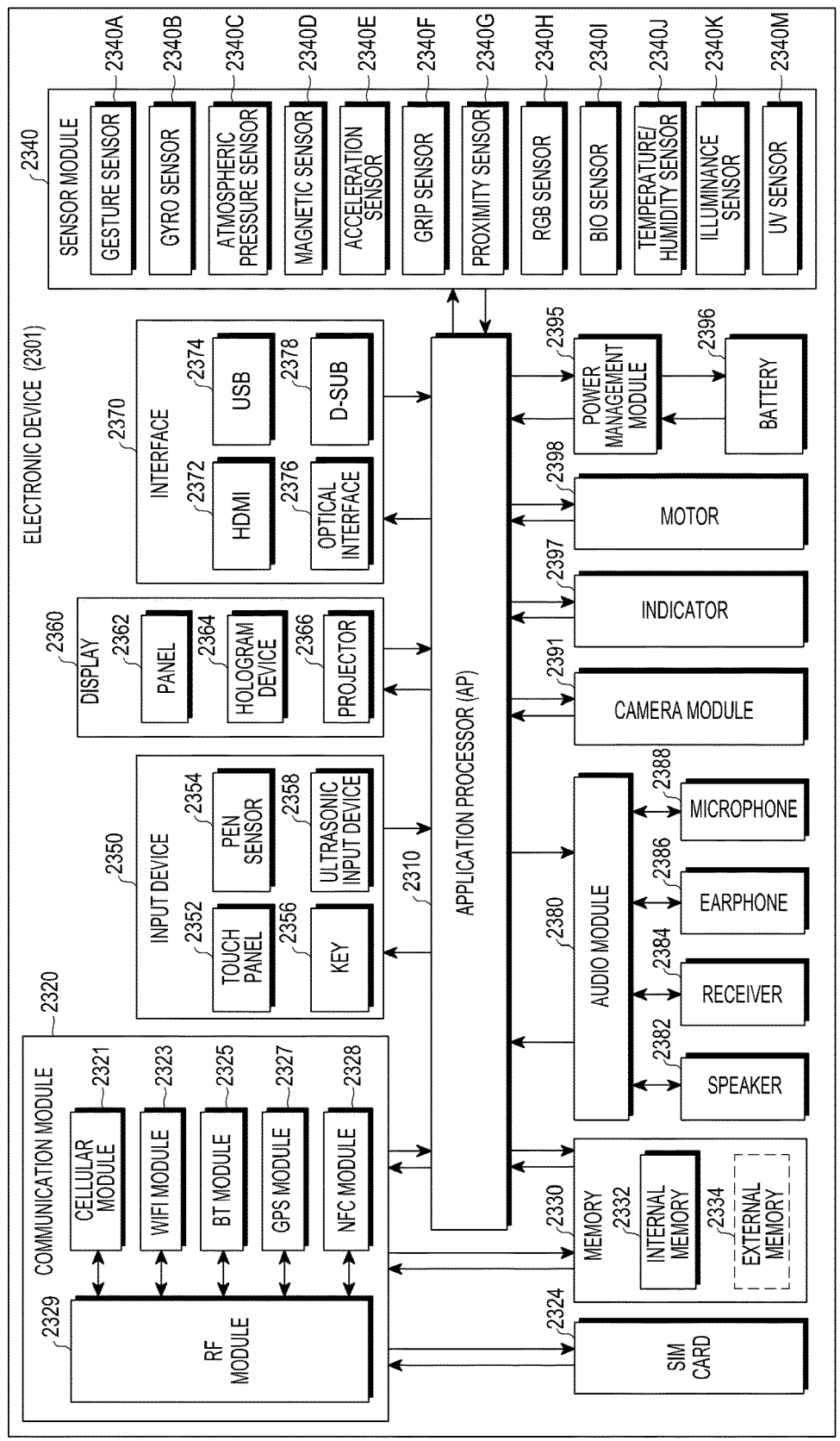
FIG. 23 is a block diagram illustrating an electronic device, according to an embodiment of the present invention.

FIG. 23 is a block diagram illustrating an electronic device 2301, according to an embodiment of the present invention. The electronic device 2301 includes the whole or part of the configuration of, e.g., the electronic device 101 shown in FIG. 1. Referring to FIG. 23, the electronic device 2301 may include one or more application processors (APs) 2310, a communication module 2320, a subscriber identification module (SIM) card 2324, a memory 2330, a sensor module 2340, an input device 2350, a display 2360, an interface 2370, an audio module 2380, a camera module 2391, a power management module 2395, a battery 2396, an indicator 2397, and a motor 2398.

The AP 2310 controls multiple hardware and software components connected to the AP 2310 by running an operating system or application programs, and the AP 2010 processes and compute various data including multimedia data. The AP 2310 may be implemented in, e.g., a System on Chip (SoC). The AP 2310 may further include a graphic processing unit (GPU).

The communication module 2320 (e.g. the communication interface 160) performs data communication with other electronic devices (e.g., the electronic device 104 or the health-care server 106) connected with the electronic device 2301 (e.g., the electronic device 101) via a network. The communication module 2320 includes a cellular module 2321, a WiFi module 2323, a BT module 2325, a GPS module 2327, an NFC module 2328, and a radio frequency (RF) module 2329.

The cellular module 2321 provides voice call, video call, text, or internet services through a communication network (e.g., an LTE, LTE-A, CDMA, WCDMA, UMTS, WiBro, or GSM network). The cellular module 2321 performs identification and authentication on the electronic device 2301 in the communication network using, e.g., a subscriber identification module (e.g., the SIM card 2324). The cellular module 2321 performs at least some of the functions providable by the AP 2310. For example, the cellular module 2321 performs at least some of the multimedia control functions.

The cellular module 2321 includes a communication processor (CP). The cellular module 2321 may be implemented in, e.g., an SoC. Although in FIG. 23 the cellular module 2321 (e.g., a communication processor), the memory 2330, or the power management module 2395 are provided separately from the AP 2310, the AP 2310 may be configured to include at least some (e.g., the cellular module 2021) of the above-listed components, according to an embodiment of the present disclosure.

The AP 2310 or the cellular module 2321 (e.g., a communication processor) loads commands or data received from a non-volatile memory or other component connected thereto and processes the loaded commands or data. The AP 2310 or the cellular module 2321 stores, in the non-volatile memory, data received from other component(s) or data generated by the other components).

The WiFi module 2323, the BT module 2325, the GPS module 2327, or the NFC module 2328 may perform a process for, e.g., processing data communicated through the module. Although in FIG. 23 the cellular module 2321, the WiFi module 2323, the BT module 2325, the GPS module 2327, and the NFC module 2328 are shown in their respective separate blocks, at least some (e.g., two or more) of the cellular module 2321, the WiFi module 2323, the BT module 2325, the GPS module 2327, and the NEC module 2328 may be included in a single integrated circuit (IC) or an IC package. For example, at least some of the processors respectively corresponding to the cellular module 2321, the WiFi module 2323, the BT module 2325, the GPS module 2327, and the NFC module 2328 (e.g., the communication processor corresponding to the cellular module 2321 and the WiFi processor corresponding to the WiFi module 2323) may be implemented in a single SoC.

The RF module 2329 communicates data, e.g., RF signals. The RF module 2329 may include, e.g., a transceiver, a power amp module (PAM), a frequency filter, or a low noise amplifier (LNA). The RF module 2329 may further include parts (e.g., conductors or wires) for communicating radio waves in a free space upon performing wireless communication. Although in FIG. 23 the cellular module 2321, the WiFi module 2323, the BT module 2325, the GPS module 2327, and the NFC module 2328 share a single RF module 2329, the cellular module 2321, the WiFi module 2323, the BT module 2325, the GPS module 2327, or the NFC module 2328 may communicate RF signals through a separate RF module(s).

The SIM card 2324 may include a subscriber identification module, and the SIM card 2324 may be inserted into a slot formed at a predetermined position of the electronic device. The SIM card 2324 may contain unique identification information (e.g., an integrated circuit card identifier (ICCID) or subscriber information (e.g., an international mobile subscriber identity (IMSI)).

The memory 2330 (e.g., the memory 130) may include an internal memory 2332 or an external memory 2334. The internal memory 2332 may include, e.g., a volatile memory (e.g., a dynamic RAM (DRAM), a static RAM (SRAM), a synchronous dynamic RAM (SDRAM), etc.) or a non-volatile memory (e.g., a one time programmable ROM (OTPROM), a programmable ROM (PROM), an erasable and programmable ROM (EPROM), an electrically erasable and programmable ROM (EEPROM), a mask ROM, a flash ROM, a NAND flash memory, or a NOR flash memory).

The internal memory 2332 may be a solid state drive (SSD). The external memory 2334 may include a flash drive, e.g., a compact flash (CF) memory, a secure digital (SD) memory, a micro-SD memory, a min-SD memory, an extreme digital (xD) memory, or a memory stick. The external memory 2334 may be functionally connected with the electronic device 2301 via various interfaces. The electronic device 2301 may further include a storage device (or storage medium) such as a hard disk drive.

The sensor module 2340 measures a physical quantity or detects an operational stage of the electronic device 2301, and the sensor module 2040 converts the measured or detected information into an electrical signal. The sensor module 2340 includes, e.g., a gesture sensor 2340A, a gyro sensor 2340B, an atmospheric pressure sensor 2340C, a magnetic sensor 2340D, an acceleration sensor 2340E, a grip sensor 2340F, a proximity sensor 2340G, a color sensor 2340H such as a red, green, blue (RGB) sensor, a bio sensor 2340I, a temperature/humidity sensor 2340J, an illuminance sensor 2340K, or an ultra violet (UV) sensor 2340M. Additionally or alternatively, the sensor module 2340 may include, e.g., an E-nose sensor, an electromyography (EMG) sensor, an electroencephalogram (EEG) sensor, an electrocardiogram (ECG) sensor, an infrared (IR) sensor, an iris sensor, or a finger print sensor. The sensor module 2340 may further include a control circuit for controlling at least one or more of the sensors included in the sensor module 2040.

The input device 2350 includes a touch panel 2352, a digital pen sensor 2354, a key 2356, or an ultrasonic input device 2358. The touch panel 2352 recognizes touch inputs using at least one of capacitive, resistive, infrared, or ultrasonic methods. The touch panel 2352 may further include a control circuit. With the capacitive method, physical contact or proximity detection may be possible. The touch panel 2352 may further include a tactile layer. In this regard, the touch panel 2352 may provide the user with a tactile response.

The digital pen sensor 2354 may be implemented in a way identical or similar to how a touch input of a user is received, or by using a separate sheet for recognition. The key 2356 may include e.g., a physical button, optical key or key pad. The ultrasonic input device 2358 may use an input tool that generates an ultrasonic signal and enables the electronic device 2301 to determine data by sensing the ultrasonic signal to the microphone 2388, thereby enabling wireless recognition. The electronic device 2301 receives the user's input from an external electronic device (e.g., a network, computer, or server) connected with the electronic device 2301 using the communication module 2320.

The display 2360 (e,g, the display 150) includes a panel 2362, a hologram device 2364, or a projector 2366. The panel 2362 may be, e.g., a liquid crystal display (LCD), active matrix organic light emitting diodes (AMOLEDs), or the like. The panel 2362 may be implemented to be flexible, transparent, or wearable. The panel 2362 may also he incorporated with the touch panel 2352 in a module. The hologram device 2364 projects three dimensional (3D) images (holograms) in the air by using light interference. The projector 2366 displays an image by projecting light onto a screen. The screen may be, for example, located inside or outside of the electronic device 2301. The display 2360 may further include as control circuit to control the panel 2362, the hologram device 2364, or the projector 2366.

The interface 2370 may include e.g., a high definition multimedia interface (HDMI) 2372, a USB 2374, an optical interface 2376, or a D-subminiature (D-sub) 2378. The interface 2370 may be included in e.g., the communication interface 1660 shown in FIG. 16. Additionally or alternatively, the interface 2370 may include a mobile high-definition link (MHL) interface, a secure digital (SD) card/multimedia card (MMC) interface, or IrDA standard interface.

The audio module 2380 performs various processes (e.g., encoding or decoding) relating to converting a sound wave and audio signal to an electric signal or vice versa. At least a part of the audio module 2380 may be included in e.g., the input/output interface 140 as shown in FIG. 1. The audio module 2380 processes sound information input or output through e.g., a speaker 2382, a receiver 2384, an earphone 2386, or a microphone 2388.

The camera module 2391 may be a device for capturing still images and videos, and may include, one or more image sensors (e.g., front and back sensors), a lens, an image signal processor (ISP), or a flash such as an LED or xenon lamp.

The power management module 2395 manages power of the electronic device 2301. Although not shown, e.g., a power management integrated circuit (PMIC), a charger IC, or a battery gauge is included in the power management module 2395.

The PMIC may be mounted on e.g., an IC or an SOC. A charging method may be divided into wired and wireless charging methods. The charger IC may charge a battery and prevent overvoltage or overcurrent from being induced from a charger. The charger IC may be used in at least one of a cable charging scheme and a wireless charging scheme. The wireless charging scheme may include e.g., a magnetic resonance scheme, a magnetic induction scheme, or an electromagnetic wave based scheme, and an additional circuit, such as a coil loop, a resonance circuit, a rectifier, or the like may be added for wireless charging.

The battery gauge measures an amount of remaining power of the battery 2396, a voltage, a current, or a temperature while the battery 2096 is being charged. The battery 2396 saves and/or generates electricity and supplies power to the electronic device 2301 with the saved or generated electricity. The battery 2396 may include, e.g., a rechargeable battery or a solar battery.

The indicator 2397 indicates a particular state of the electronic device 2301 or a part of the electronic device 2301

(e.g., the AP 2310), including e.g., a booting state, a message state, or recharging state. The motor 2398 converts an electric signal to a mechanical vibration. Although not shown, a processing unit for supporting mobile TV, such as a GPU may be included in the electronic device 2301. The processing unit for supporting mobile TV may process media data conforming to a standard for digital multimedia broadcasting (DMB), digital video broadcasting (DVB), or media flow.

Each of the aforementioned components of the electronic device 2301 may include one or more parts, and a name of the part may vary with a type of the electronic device. The electronic device 2301 may include at least one of the aforementioned components, omit some of them, or include other additional component(s). Some of the components may be combined into an entity, but the entity may perform the same functions as the components may do.

At least a part of the device (e.g., modules or their functions) or method (e.g., operations) may be implemented as instructions stored in a non-transitory computer-readable storage medium e.g., in the form of a programming module. The instructions, when executed by one or more processor (e.g., the processor 1610), enables the one or more processors to carry out a corresponding function. The non-transitory computer-readable storage medium may be e.g., the memory 2330. At least a part of the programming module may be implemented (e.g., executed) by e.g., the processor 2320. At least a part of the programming module may include e.g., a module, program, routine, set of instructions, process, or the like for performing one or more functions.

The non-transitory computer-readable storage medium may include a hardware device configured to store and perform program instructions (e.g., programming module), such as magnetic media such as hard discs, floppy discs, and magnetic tapes, optical media such as Compact Disc ROMs (CD-ROMs) and Digital Versatile Discs (DVDs), magneto-optical media such as floptical disks, ROMs, RAMs, Flash Memories, and/or the like. Examples of the program instructions may include not only machine language codes but also high-level language codes which are executable by various computing means using an interpreter. The aforementioned hardware devices may be configured to operate as one or more software modules to carry out embodiments of the present invention, and vice versa.

Modules or programming modules in accordance with various embodiments of the present invention may include at least one or more of the aforementioned components, omit some of them, or further include other additional components. Operations performed by modules, programming modules or other components in accordance with various embodiments of the present invention may be carried out sequentially, simultaneously, repeatedly, or heuristically. Furthermore, some of the operations may be performed in a different order, or omitted, or include other additional operation(s).

Various embodiments of the present invention may be implemented in hardware, software, or a combination of hardware and software. Such software may be stored in a volatile or non-volatile storage device such as a read-only memory (ROM) or other storage devices, a memory, such as a random access memory (RAM), a memory chip, a device or an integrated circuit, or a storage medium, such as, e.g., a compact disk (CD), a digital video disk (DVD), a magnetic disk, or a magnetic tape, which allows for optical or magnetic recording while simultaneously read out by a machine (e.g., a computer). The storage unit that may be included in the electronic device 2301 may be an example of a storage medium that may be read out by a machine appropriate to store a program or programs including instructions for realizing the embodiments of the present invention. Accordingly, various embodiments of the present invention encompass a program containing codes for implementing the device or method set forth in the claims of this disclosure and a machine-readable storage medium storing the program. The program may be electronically transferred via any media such as communication signals transmitted through a wired or wireless connection and various embodiments of the present invention properly include the equivalents thereof.

The electronic device 2301 may receive the program from a program providing device wiredly air wirelessly connected thereto and store the same. The program providing device may include a memory for storing the program including the instructions for performing a method for enhancing accuracy when the electronic device 2301 performs contactless body temperature measurement, a communication unit for performing wired or wireless communication with the electronic device 2301, and a controller that may transmit the program to the electronic device automatically or in response to a request from the electronic device.

As is apparent from the forgoing description, according to various embodiments of the present invention, a contactless body temperature measurement function is implemented in the electronic device 2301, so that the electronic device 2301 can be carried while allowing for precise body temperature measurement, away from the portion of an body at which a temperature is to be measured at a predetermined distance, thus enhancing user convenience.

According to various embodiments of the present invention, the camera focal distance function equipped in the electronic device 2301 may be used to enable measured body temperature values to be obtained with the distance between the body temperature measurement sensor and the object whose temperature is to be measured remaining constant for each body temperature measurement, thus reducing measurement errors due to variations in the measurement distance and enhancing accuracy.

Further, according to various embodiments of the present invention, the user may identify the position of measurement and whether there is interference from foreign substances using images captured by the camera, thus reducing measurement errors.

Further, according to various embodiments of the present invention, heterogeneous wireless communication-enabled electronic devices may be linked with each other in use, thereby allowing the user to measure body temperature while observing the images of the portion of the body at which a temperature is to be measured displayed on the electronic device. Accordingly, the portion of the body at which a temperature is to be measured and whether there are interfering substances on the portion of the body may be easily identified, thereby preventing measurement errors due to the foreign substances and allowing measurement results to be easily obtained simultaneously with measurement.

While the present invention has been shown and described with reference to certain embodiments thereof, it should be understood by those skilled in the art that many variations and modifications of the method and apparatus described herein will still fall within the spirit and scope of the present invention as defined in the appended claims and their equivalents.

What is claimed is:

1. An electronic device for enhancing accuracy of a contactless body temperature measurement for an object, the electronic device comprising:
   a camera module;
   a contactless temperature sensor; and
   a processor configured to:
   control the camera module to obtain images for a portion of the object,
   control the contactless temperature sensor to continuously measure temperatures for the portion of the object;
   identify, from among the images for the portion of the object, an image in focus, wherein the image in focus is taken when the portion of the object is positioned at a predetermined distance from the camera module;
   identify, from among the measured temperatures, a temperature associated with the identified image in focus; and
   determine the identified temperature as a temperature of the object,
   wherein the camera module and the contactless temperature sensor are disposed on a same surface, which faces the portion of the object, of the electronic device.

2. The electronic device of claim 1, wherein the images for the portion of the object are taken by the camera module in a macro mode of the camera module; and
   wherein the images for the portion of the object are images for at least one of a portion of a forehead of a human being where a temporal artery of the human being is distributed and a portion from behind an ear lobe of the human being where the temporal artery passes.

3. The electronic device of claim 1, wherein the processor controls a display to display the images for the portion of the object and a measurement result including the determined temperature of the object.

4. The electronic device of claim 1, further comprising a communication interface for connecting the electronic device to another electronic device via a short-range wireless communication scheme and transmitting a measurement result including the determined temperature of the object to the another electronic device for displaying the measurement result including the determined temperature of the object on a screen of the another electronic device.

5. The electronic device of claim 1, wherein the camera module and the contactless temperature sensor are activated when an application for measuring body temperature is executed on the electronic device.

6. The electronic device of claim 1, wherein the processor controls the contactless temperature sensor to measure the temperature for the object when the image being in focus is taken by the camera module.

7. The electronic device of claim 1, wherein the contactless temperature sensor continuously measures a temperature for the portion of the object while the images for the portion of the object are taken by the camera module.

8. The electronic device of claim 1, wherein the processor outputs an instruction to the user of the electronic device indicating that a distance between the electronic device and the object needs to be adjusted.

9. The electronic device of claim 1, wherein the processor determines, using the images for the portion of the object, whether there is a foreign substance in the image for the object, and if it is determined that there is a foreign substance, outputs an instruction to the user requesting removal of the foreign substance.

10. The electronic device of claim 1, wherein the contactless temperature sensor is an infrared sensor that measures, at the predetermined distance from the object, a temperature for the portion of the object.

11. The electronic device of claim 10, wherein the predetermined distance is equal to a focal length between the camera module and a portion of the object.

12. The electronic device of claim 1, wherein the processor adjusts a position of measurement by determining whether the images for the portion of the object include a shape of at least a portion of an eyebrow.

13. The electronic device of claim 1, wherein the processor adjusts a position of measurement by determining whether the images for the portion of the object include a shape of at least a portion of an ear.

14. A method for enhancing accuracy of a contactless body temperature measurement by an electronic device, the electronic device comprising a camera module, a contactless temperature sensor and a processor, the method comprising:
   obtaining images for a portion of an object from the camera module;
   continuously measuring, by the contactless temperature sensor, temperatures for the portion of the object;
   identifying, from among the images for the portion of the object, an image in focus, wherein the image in focus is taken when the portion of the object is positioned at a predetermined distance from the camera module;
   identifying, from among the measured temperatures, a temperature associated with the identified image being in focus;
   determining the identified temperature as a temperature of the object; and
   displaying the temperature of the object.

15. The method of claim 14, wherein the images for the portion of the object are obtained by the camera module in a macro mode of the camera module, and
   wherein the images for the portion of the object are images for at least one of a portion of a forehead of a human being where a temporal artery of the human being is distributed and a portion from behind an ear lobe of the human being where the temporal artery passes.

16. The method of claim 14, further comprising:
   measuring the temperature for the object when the image being in focus is taken by the camera module.

17. The method of claim 14, further comprising:
   continuously measuring, by the contactless temperature sensor, a temperature for the portion of the object while the images for the portion of the object are taken by the camera module.

18. The method of claim 14, wherein the measured temperature for the portion of the object is a temperature measured by radiating, at the predetermined distance from the object, an infrared signal at the object.

19. The method of claim 14, wherein the predetermined distance is equal to a focal length between the camera module and the portion of the object.

20. The method of claim 14, further comprising displaying a preview of the image for the portion of the object when an application for measuring contactless temperature is executed on the electronic device.

21. The method of claim 14, further comprising:
   connecting the electronic device with another electronic device via a short-range wireless communication scheme; and
   transmitting the measured temperature for the portion of the object to the another electronic device for displaying the measured temperature for the portion of the object on a screen of the another electronic device.

22. The method of claim 14, further comprising outputting an instruction indicating that a distance between the electronic device and the object needs to be adjusted.

23. The method of claim 14, further comprising:
   determining, using images for the portion of the object, whether there is a foreign substance on the image; and
   if it is determined that there is a foreign substance, outputting an instruction to the user requesting removal of the foreign substance.

24. The method of claim 14, further comprising adjusting a position of measurement by determining whether the images for the portion of the object include a shape of at least a portion of an eyebrow.

25. The method of claim 14, further comprising adjusting a position of measurement by determining whether the images for the portion of the object include a shape of at least a portion of an ear.

\* \* \* \* \*